(12) United States Patent
Akhbardeh et al.

(10) Patent No.: US 11,963,793 B2
(45) Date of Patent: Apr. 23, 2024

(54) REAL-TIME TRACKING OF CEREBRAL HEMODYNAMIC RESPONSE (RTCHR) OF A SUBJECT BASED ON HEMODYNAMIC PARAMETERS

(71) Applicant: ROPAMedics LLC, San Francisco, CA (US)

(72) Inventors: Alireza Akhbardeh, Redwood City, CA (US); Amir Tehrani, San Francisco, CA (US)

(73) Assignee: ROPAMEDICS LLC, San Francisco, CA (US)

( * ) Notice: Subject to any disclaimer, the term of this patent is extended or adjusted under 35 U.S.C. 154(b) by 594 days.

(21) Appl. No.: 16/557,663

(22) Filed: Aug. 30, 2019

(65) Prior Publication Data

US 2020/0093427 A1     Mar. 26, 2020

Related U.S. Application Data

(63) Continuation of application No. 14/203,987, filed on Mar. 11, 2014, now abandoned.

(60) Provisional application No. 61/776,527, filed on Mar. 11, 2013.

(51) Int. Cl.
*A61B 5/00* (2006.01)
*A61B 5/01* (2006.01)
*A61B 5/1455* (2006.01)
*A61B 5/369* (2021.01)

(52) U.S. Cl.
CPC .............. *A61B 5/4824* (2013.01); *A61B 5/01* (2013.01); *A61B 5/14553* (2013.01); *A61B 5/369* (2021.01); *A61B 2562/0219* (2013.01)

(58) Field of Classification Search
CPC .............. A61B 2562/0219; A61B 5/01; A61B 5/14553; A61B 5/369; A61B 5/4824
See application file for complete search history.

(56) References Cited

U.S. PATENT DOCUMENTS

| | | | |
|---|---|---|---|
| 5,309,907 A | 5/1994 | Fang et al. | |
| 5,713,352 A | 2/1998 | Essenpreis et al. | |
| 6,553,242 B1* | 4/2003 | Sarussi | A61B 5/6829 600/323 |
| 6,654,622 B1* | 11/2003 | Eberhard | A61B 5/6816 600/326 |
| 8,382,666 B1* | 2/2013 | Mao | G02B 6/4219 600/202 |

(Continued)

FOREIGN PATENT DOCUMENTS

WO      2010/134068 A1     11/2010

OTHER PUBLICATIONS

Bing El U. et al., Somatotopic organization of human somatosensory cortices for pain: a single trial fMRI study, NeuroImage 23 (2004) pp. 224-232.

(Continued)

*Primary Examiner* — Jonathan T Kuo
*Assistant Examiner* — Vynn V Huh
(74) *Attorney, Agent, or Firm* — Venable LLP; Henry J. Daley

(57) ABSTRACT

A system for measuring pain of a person, the system for use with the tissue of the person. Various sensors and detectors on the tissue provide signals to a controller for determining and indicating a pain level of the person.

8 Claims, 17 Drawing Sheets

(56) References Cited

U.S. PATENT DOCUMENTS

| | | | |
|---|---|---|---|
| 8,512,240 B1* | 8/2013 | Zuckerman-Stark | G16H 50/20 128/924 |
| 8,814,791 B2 | 8/2014 | Sethi et al. | |
| 8,930,145 B2 | 1/2015 | Li et al. | |
| 9,153,112 B1* | 10/2015 | Kiani | A61B 5/02438 |
| 2003/0069486 A1* | 4/2003 | Sueppel | A61B 5/14551 600/322 |
| 2005/0234319 A1 | 10/2005 | Mandelis et al. | |
| 2008/0091089 A1 | 4/2008 | Guillory et al. | |
| 2011/0137297 A1* | 6/2011 | Kiani | A61B 5/4821 604/890.1 |
| 2011/0245633 A1 | 10/2011 | Goldberg et al. | |
| 2012/0083673 A1 | 4/2012 | Al-Ali et al. | |
| 2012/0130203 A1 | 5/2012 | Stergiou et al. | |
| 2012/0132211 A1 | 5/2012 | Halperin et al. | |
| 2014/0073900 A1 | 3/2014 | Wood et al. | |

OTHER PUBLICATIONS

Bouma, GJ et al., "Relationship between cardiac output and cerebral blood flow in patients with intact and with mpaired autoregulation", J. Neurosurg. Sep. 7, 19903(3), pp. 368-374, Abstract only.

Brown, Justin E. et al., Towards a Physiology-Based Measure of Pain: Patterns of Human Brain Activity Distinguish Painful from Non-Painful Thermal Stimulation, Plos One, www.plosone.org, vol. 6, Issue 9, Sep. 2011, 8 pages.

Elgendi, Mohamed, "On the Analysis of Fingertip Photoplethysmogram Signals", Current Cardiology Reviews, 2012, vol. 8, No. 1, pp. 14-25.

Extended European Search Report dated Oct. 12, 2016 relating to European Patent Application No. 14779148.7, 7 pages.

Ferrari, Marco et al., "A brief review on the history of human functional near-infrared spectroscopy (fNIRS) development and fields of application", NeuroImage (2012), 15 pages.

Ferrari, Marco et al., Principles, Techniques, and Limitations of Near Infrared Spectroscopy, Can. J. Appl. Physiol., 2004, 29(4) pp. 463-487.

Flor, H. et al., "Chronic Pain: An Integrated Biobehavioral Approach", Cognitive and Behavioral Practice 20 (2013) pp. 117-118.

Frolich, Michael A. et al., "Quantitative Changes in Regional Cerebral Blood Flow induced by Cold, Heat and Ischemic Pain: A Continuous Arterial Spin Labeling Study", Anesthesiology, Oct. 2012, 117(4), 20 pages.

Galante, Nicholas Joseph, "Photoplethysmographic Waveform Analysis During Lower Body Negative Pressure Simulated Hypovolemia as a Tool to Distinguish Regional Differences in Microvascular Blood Flow Regulation", Sep. 14, 2009, Yale Medicine Thesis Digital Library, 57 pages.

Izzetoglu et al., "The evolution of field deployable fNIR spectroscopy from bench to clinical settings", Journal of Innovative Optical Health Sciences, vol. 4, No. 3 (2011) 239-250.

Moerman, A. et al., "Near-infrared spectroscopy {NIRS) monitoring in contemporary anesthesia and critical care", Acta Anaesth. Belg. 2010, 61, pp. 185-194.

Oppenheim Alan V. et al., Discrete-Time Signal Processing (Second Edition), Prentice Hall, Upper Saddle River, New Jersey (1999), 894 pages (Uploaded to EFS as two attachments, Attachment 1 pp. 1-510, Attachment 2—pp. 511-870).

Oppenheim, Alan V. et al., IIR Filters, EGE 2610 Signals and Systems (Time-Domain Response), Pearson Education, Chapter 8 (1998), 48 pages.

Photoplethysmography (PPG) system, Geer! Langereis, Version 2, Feb. 2010, 22 pages.

Reisner, Andrew et al., "Utility of the Photoplethysmogram in Circulatory Monitoring", Anesthesiology 2008, 108, pp. 950-958.

Shelley, Kirk & Shelley, S. "Pulse Oximeter Waveform: Photoelectric Plethysmography", Clinical Monitoring: Practical Applications for Anesthesia and Critical Care., (2001 ), 420-423.

Son, Il-Young et al., Near Infrared Imaging and Spectroscopy for Brain Activity Monitoring, Advances in Sensing with Security Applications, NATO Security Through Science Series vol. 2, 2006, pp. 341-372.

Steiglitz K et al., A. Technique for the Identification of Linear Systems, IEEE Transactions on Automatic Control, vol. AC-10, No. 4, Oct. 1965, pp. 461-464.

Townsend, Neil, Pulse Oximetry, Medical Electronics, Michaelmas Term 2001, pp. 32-42.

Tracey, I., Imaging Pain, British Journal of Anaesthesia 101{1 ): 32-9 (2008), pp. 32-39.

Treister et al. "Differentiating between heat pain intensities: The combined effect of multiple autonomic parameters", Apr. 9, 2012, PAIN, 153 (2012) 1807-1814.

Unknown, FOIRE-3000 Near-Infrared Brain Function Imaging System, Shimadzu Corporation, www.shimadzu.com/an/lifescience/imaging/nirs/foire.html, Oct. 1, 2012, 2 pages.

Wager, Tor D. et al., "Predicting Individual Differences in Placebo Analgesia: Contributions of Brain Activity during Anticipation and Pain Experience", The Journal of Neuroscience, Jan. 12, 2011, 31 (2), pp. 439-452.

Xu Cui, Near Infrared Spectroscopy (NIRS): List of Manufactures, www.aliv_elearn.net/?p=1335, Oct. 1, 2012, 14 pages.

* cited by examiner

REAL-TIME TRACKING OF CEREBRAL HEMODYNAMIC RESPONSE (RTCHR) OF A SUBJECT BASED ON HEMODYNAMIC PARAMETERS

CROSS-REFERENCE TO RELATED APPLICATIONS

This application is a continuation of U.S. patent application Ser. No. 14/203,987, filed Mar. 11, 2014, which is based on and claims priority from U.S. Provisional Patent Application Ser. No. 61/776,527, filed Mar. 11, 2013.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND

The present invention is in the medical field of blood flow and brain activity monitoring including hemodynamic measurement. More specifically, the present invention is in the medical, person management, animals and pets management, and pharmaceutical management fields of measuring blood flow and cerebral hemodynamic changes and impacts associated with several sensory stimuli including pain, brain injury, other neurological disorders, and anesthesia as well as others.

Measurement of pain can include a subjective component when a person's mood, culture, and other sociological, psychological, and other factors contribute to sensation and reporting of pain. Some persons like neonates, infants, children, Alzheimer persons, and/or persons under anesthesia, or in an ICU, have no mechanism of self-reporting. Also, if pain progression could be measured and a threshold set, early intervention could minimize pain progression. This is also true for persons with migraine or cluster headaches and other pains.

Pain management and treatment solutions rely on subjective data. As a result, persons are either over-medicated or under treated. Stimulation devices for treatment of pain could deliver more appropriate therapy if the stimulation level was correlated to objective, independent, reliable, and repeatable pain measurement. The evaluation and treatment of persons occurs because many may not be able to self-report their health condition, and the typical behavioral signs may be subtle or absent.

SUMMARY

In one form, a system according to embodiments of the invention indicates pain or a surrogate of pain symptoms of a person and is for use with the tissue of the person. A light source is adapted for illuminating the tissue of the person. An optical sensor is adapted for sensing light emitted or reflected by the tissue of the person. The optical sensor generates a light signal indicative of a light parameter of the sensed light. A surface electrode is adapted for sensing an electrical parameter of the tissue of the person. The surface electrode generates an electrode signal indicative of an electrical parameter of the sensed electrical parameter. A temperature sensor is adapted for sensing a temperature of the tissue of the person. The temperature sensor generates a temperature signal indicative of the sensed temperature. One or more circuits is adapted for receiving the light signal, the electrode signal, and the temperature signal and provides corresponding signals. A controller is adapted for receiving and processing the corresponding signals and is adapted for providing a pain indication signal which is a function of the corresponding signals. An indicator is adapted to be responsive to the controller for providing an indication which is indicative of the pain indication signal. A power supply supplies power to the system.

A system for cerebral monitoring of a person and a method for providing an indication of pain of a person such as measuring pain or a surrogate of pain symptoms of a person are also presented.

BRIEF DESCRIPTION OF THE DRAWINGS

FIG. 10A illustrates the oxygen saturation (SpO2) calculation. FIG. 10B illustrates pre and post processing steps to calculate heart/respiration rates and estimate hemodynamic response changes in real-time.

DETAILED DESCRIPTION

Figure 1:
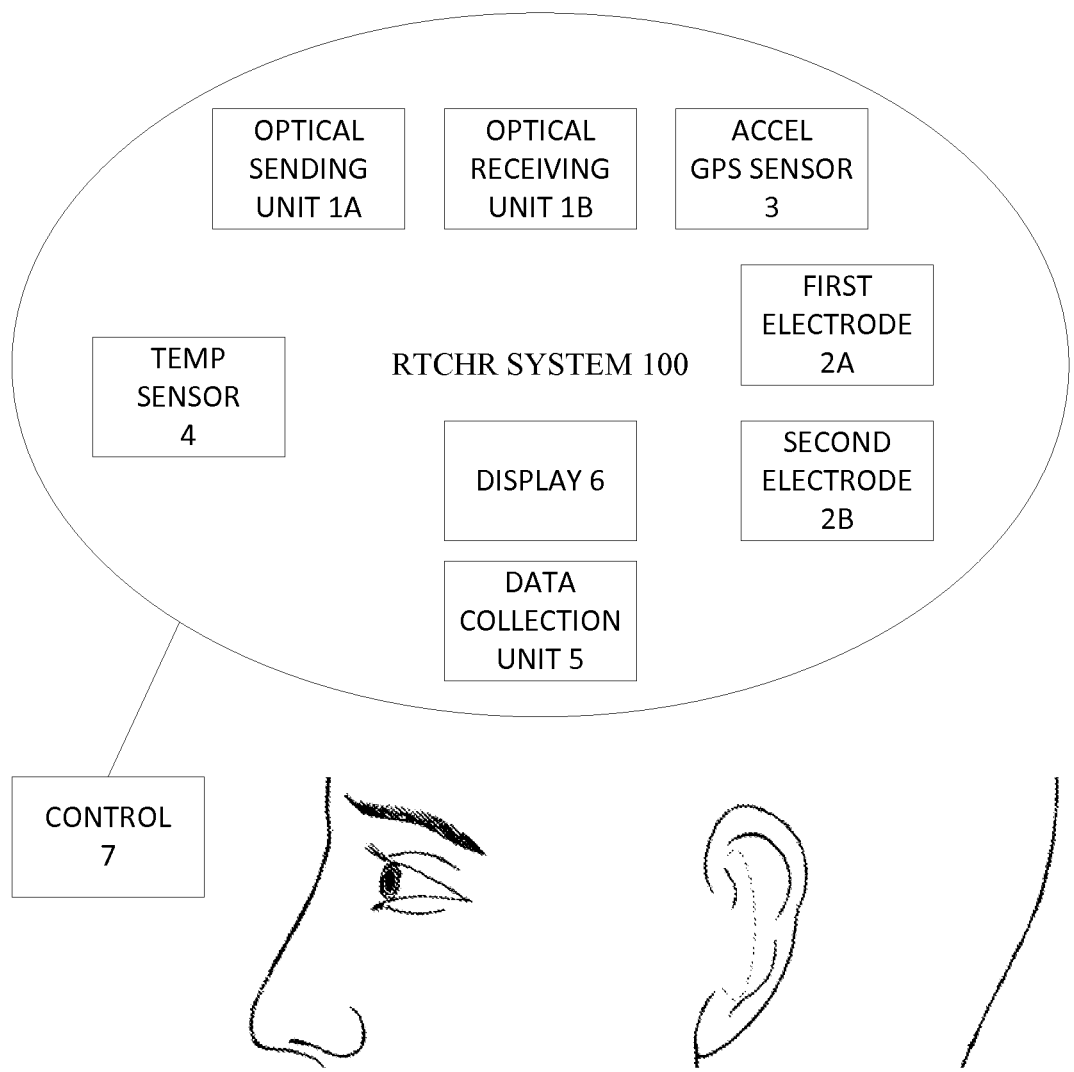
FIG. 1 illustrates a sensor system according to the system and method and a plurality of exemplary locations for the placement of the sensor system on a person's forehead.

Vital signs should not be used as primary indicators of person health condition, but rather vital signs should be considered as a cue to begin further assessment. Other than vital signs, human brain reactivity to external/internal stimuli such as pain and anesthesia has been extensively studied with the use mainly of magnetic resonance imaging and positron-emission tomography. However, the use of these sophisticated methods may be unrealistic as an affordable and ambulatory product for everyday use. Of interest to assessing these persons in a clinical and non-clinical setting is the noninvasive measurement of regional cerebral tissue oxygenation with the pulse oximetry, EEG, and near-infrared spectroscopy (NIRS) techniques. An objective of this invention is to develop cheaper techniques of detecting the cerebral hemodynamic characteristics and changes associated with sensory stimuli, including pain and anesthesia, among others. An objective of this invention is to develop a device for real-time profiling and detection of the cerebral hemodynamic patterns and changes on an ambulatory and non-ambulatory subjects using fully automatic and advanced machine learning techniques. Also provided is a system that can communicate and provide person feedback with healthcare professionals or persons to adjust the therapy or adjust other interventions.

The present invention includes a device and method for a real-time profiling, pattern recognition, and tracking of the cerebral hemodynamic changes of persons (ambulatory and/or non-ambulatory) using automatic and advanced machine learning techniques to process biological data collected using a sensor patch or a series of sensors (e.g., red and infrared lights transmitters, and/or electroencephalography—EEG, and not limited to other sensors such as accelerometers, position sensor, impedance sensor, and the like).

In an embodiment, a device could be designed and used for neonatal persons where a baseline is created and deviation from brain hemodynamics and/or other sensor parameters could alarm the nurse of infants' discomfort which could lead to pain progression or distress. The device could be a patch with wireless data communication capability. The device could transmit and receive data from the hospital monitor. The device could also include visual, audio, or electronic feedback such as colored LEDs, alarm, or data transmission to inform the hospital staff or parents of the pain or stress status of the person.

In another embodiment, the device could include an optional microphone (122; see FIG. 1A) to record neonates crying and distress levels. The device could also simultaneously detect and measure the hemodynamic or other sensors levels to define a pain or cry threshold. Such a device could be programmed to alarm the hospital staff and parents that the neonate is progressing toward higher levels of pain and distress. Therefore, an intervention could be applied before the neonate reached a maximal pain or distress level.

In yet another embodiment, a device could be designed and developed for persons under anesthesia undergoing surgery. These persons have no capability to report pain. Similar to the previously described device, a profile and threshold of the hemodynamic and other sensors could be established even prior to surgery when the person is awake and continue to record sensor measurements during surgery. If a device detects deviation from the anesthesia baseline that indicates pain or consciousness, the anesthesiologist could adjust the drug levels to comply with device trending and recommendation. This device could be a patch that also includes communications and person feedback, which can also be integrated with hospital monitoring systems. In yet another embodiment, a device could command the anesthesiologist or the anesthesia machine to deliver additional drugs to minimize pain or sensors information deviation measured by the device. In an embodiment, all devices could be disposable or reusable.

In another embodiment, a device could be worn by an ambulatory, non-ambulatory, or mobile person where the pain management device directly communicates with a control device. The control device could be a pager, a mobile phone with an app, or other variation. The control device could be programmed to request a measurement from the hemodynamic measurement device. This measurement could be programmed on hourly, daily, or other intervals. The person himself could request for an objective pain measurement through use of the mobile device. If the patch senses deviation from a baseline or emergence of pain is imminent, while it takes the objective measurements, it could send a signal to the mobile device and request the person to include his subjective level of pain. Such simultaneous objective and subjective pain measurement data could be matched and used for better treatment of the person. Persons could be alarmed of a baseline deviation and a potential for the emergence or an increase in pain sensation. For example, it is understood if migraine pain is detected early before reaching debilitating levels, persons can immediately intervene with medication and or make a change in their environment to minimize pain progression. Such a device could be a non-invasive patch or an implantable device placed under the hair, in forehead, or another part of the head and neck. This device could be a very thin and invisible device. Such a device is capable of measurements on-demand, objective, and subjective pain, and other sensor data.

Given different body positions could lead to a different type of pain (i.e., low back while standing is sensed more than lying down). In an embodiment, the device includes a position sensor. The device could also include a GPS sensor as certain environments and/or movements could lead to higher level pain inducement or sensation.

Such a device could also be used to measure a person's compliance with medications of other therapies. The mobile device could remind the person of taking medications on time and, within a given interval of time, measure changes in objective pain measurements to learn if the medication was effective. Physicians can also program and/or receive information about person objective, or subjective pain levels and medication of other therapy compliance. Physicians could also command pain level measurements both objective from the patch and subjective from the mobile device app and the person. The received information could be used for treatment titration and compliance improvement.

The device and method could also include communications in the form of a Q&A with the person to better categorize pain, mood, stress, emotional, and behavioral variations in sensor measurements level. The sensors results could be matched with a person's conditions and/or environments to therefore provide improved person pain management. Thus, the objective sensor measurement may be combined, synchronized, and/or aligned with a person's subjective input in a variety of environments.

It is contemplated that at least some embodiments of the devices or methods of the invention could be implemented to aid in reducing addictions to opiates medication, i.e., narcotics and pain killers such as Oxycontin™ (oxycodone HCl). Addiction to opiate drugs are increasing at alarming rates and causing significant issues to the healthcare system including rising costs, suicides, and dependencies. However, if these drugs are administered when the patient really needs it rather than at a prescribed rate, there is a possibility to reduce dependencies.

It is contemplated that at least some embodiments of the devices or methods of the invention could also help to self-discipline or discipline patients to administer/consume the medications when there is significant pain on the horizon. The predictability of rising pain levels based on history of a patient could help with minimizing the required medication to treat the pain at an early onset. Therefore, at least some embodiments of the devices or methods of the invention could minimize required medications for the treatment of pain.

In today's subjective pain measurement, a person is asked to rate the pain level from 1-10 in a doctor's office or another location. The same format of subjective pain measurements, Q&A, or other approaches can be combined into a mobile APP and synchronized with the measurement by the system of the invention or vice versa. A person may feel more pain in one environment or position vs. another. The system may measure the same pain level but the person's perception could be different at a different environment. The system will identify these differences or changes and create different profiles related to mood, stress, environment, and/or positions to help with person management. For example, one environment may require increased pain medication to alleviate pain. Therefore, the device will be intelligent enough to provide proper information to the person. Besides measurement and monitoring of pain, this device could be used for managing a brain injury, for diagnosis of a brain injury as well as used for sleep apnea diagnosis.

The real-time tracking of cerebral hemodynamic response (RTCHR) optical technology systems, unlike pulse oximetry, uses chirp modulation in the hardware to measure the level of hemoglobin oxygenation ("oxy Hb"). The RTCHR technology is also different than spectroscopy because spectroscopy requires several wavelengths of light. The pulse oximeter uses the property that oxyhemoglobin and deoxyhemoglobin absorb light of different wavelengths in a specific way. A light source is provided to sequentially pass light of different wavelengths through a sample of oxy Hb. A detector determines the amount of light, at each wavelength, has been absorbed. Pulse oximetry uses two wavelengths (i.e., 650 and 950 nm). One is a red light, which has a wavelength of approximately 650 nm. The other is an infrared light, which has a wavelength of 950 nm. The pulse oximeter determines the oxygen saturation by comparing the amount of red light and infra-red light are absorbed by the blood. Depending on the amounts of oxy Hb and deoxy Hb present, the ratio of the amount of red light absorbed compared to the amount of infrared light absorbed changes.

Functional Near-Infra-Red Spectroscopy (fNIRS) uses a similar approach, but it looks at all waveforms in a near infra-red field. Further, fNIRS uses the near-infrared region of the electromagnetic spectrum (i.e., from about 800 nm to 2500 nm). Typical applications include pharmaceutical, medical diagnostics (including blood sugar and blood oxygenation), food and agrochemical quality control, and combustion research, as well as research in functional neuroimaging, sports medicine & science, elite sports training, ergonomics, rehabilitation, neonatal research, brain computer interface, urology (bladder contraction), and neurology (neurovascular coupling). In NIRS, multiple LED senders and receivers with different wavelength/light settings are used to get light reflection at different wavelengths. To get more spectrum data at more wavelengths, more LED sensors and receivers are needed. This dramatically increases the price of the NIRS, and it increases complexity of hardware and software.

In the present invention, lights with different wavelengths are induced over time using frequency modulation (chirp profile) to fit the need of a specific person or obtain most accurate hemodynamic measurements. In this approach, multiple LEDs are not needed, and the invention only needs one pair LED transceivers and different lights are induced over time using chirp frequency excitation of LEDs (see FIG. 3). This will make RTCHR technology different than current pulse oximetry and existing NIRS devices, which need multiple LED senders/receivers. This will make the technology inexpensive compared to NIRS and compatible to the cost of a pulse oximetry device.

In an embodiment, the device includes the correlation of presence and level of pain with heart rate, temperature, brain activity, blood pressure, or vice versa. The system measures all these parameters simultaneously and can analyze the data to identify patterns and intelligence. The system could also correlate pain level to certain positions, activity levels, and/or locations/environments.

The system could be used for human and animal subjects as well. Pet owners have significant interests to know if their pets are experiencing pain, and if the pain management and treatment is effective. Therefore, another variation of this device could be designed and developed to fit certain pet specifies. The system could be used for drug/pharmaceutical development purposes as well.

Referring now to the invention in more detail, FIG. 1 shows a lateral view of the face and location of a real-time tracking of cerebral hemodynamic response (RTCHR) patch system 100 for real-time tracking of cerebral hemodynamic response changes on an ambulatory subject. It records hemodynamic response changes, heart rate, respiration, and Electroencephalogram (EEG). To localize hemodynamic response and estimate stimulus type, one or more additional patch systems 100 positioned on the forehead, on the skull or other part of body can be used. In FIG. 1

1) Optical sender/receiver unit 1A, 2B.
2) Standard Surface electrode 2A, 2B.
3) Accelerometer/GPS sensor 3.
4) Temperature sensor 4.
5) Data acquisition unit 5 to fetch data from sensors, apply any necessary filtering, convert the sensor data in a form for transmission to a control 7, and transmit recorded sensor data via wired or wireless transmission to the control 7.

6) Display 6 such as LCD/LEDs on the patch system 100 to display pain level and heart/respiration rates.

7) Control 7 fetches sensor data via wired or wireless transmission line and applies necessary signal processing and machine learning techniques to estimate hemodynamic parameters in real-time while subject can do his/her normal daily activities. It then displays the hemodynamic parameters and stores raw and estimated results in a dedicated server. The control box could be stand-alone or integrated with patch.

Figure 1A:
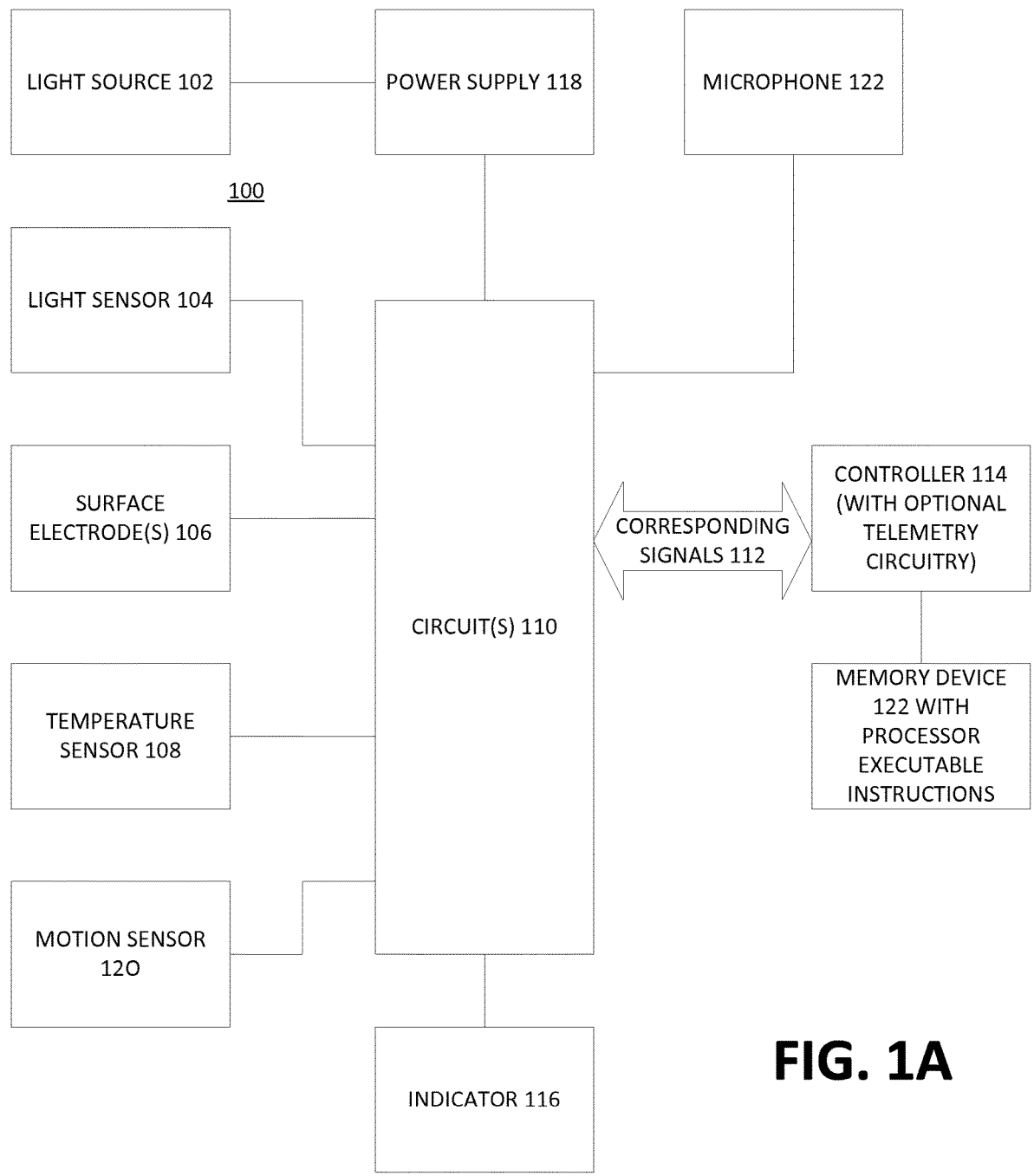
FIG. 1A is block diagram illustrating a system and method.

FIG. 1A is block diagram illustrating a RTCHR system 100 and method. The system 100 measures pain of a person and is for use with the tissue (e.g., skin) of the person. A light source 102 is adapted for illuminating the tissue of the person. An optical sensor 104 is adapted for sensing light emitted or reflected by the tissue of the person. The optical sensor 104 generates a light signal indicative of a light parameter of the sensed light. The light signal is indicative of pulse oxygen levels, respirations and heart rate.

A surface electrode 106 is adapted for sensing an electrical parameter of the tissue of the person. The surface electrode 106 generates an electrode signal indicative of an electrical parameter of the sensed electrical parameter. The electrode signal is indicative of heart rate, sweat and respirations.

A temperature sensor 108 is adapted for sensing a temperature of the tissue of the person. The temperature sensor 108 generates a temperature signal indicative of the sensed temperature. The temperature signal is indicative of body temperature.

One or more circuits 110 are adapted for receiving the light signal, the electrode signal, and the temperature signal and providing corresponding signals 112. The circuits 110 apply any necessary filtering, convert the sensor data in a form for transmission to a controller 114, and transmit recorded sensor data via wired or wireless transmission to the control 114. Thus, in one embodiment, the controller 114 includes optional telemetry circuitry to communicate with other devices. For example, the controller 114 may communicate with a mobile device such as a cell phone or hospital monitor and provide information indicative of the signals to the mobile device. The controller 114 is adapted for receiving and processing the corresponding signals and is adapted for providing a pain indication signal which is a function of the corresponding signals. An indicator 116 is adapted to be responsive to the controller 114 for providing an indication which is indicative of the pain indication signal pain signal such as a signal indicative of measured pain or indicative of a surrogate of pain symptoms. [Herein, the pain indication signal is also referred to as a pain signal.]. A power supply 118 supplies power to the system.

A motion sensor 120 is adapted for sensing a motion of the person. The motion sensor 120 generates a motion signal indicative of the sensed motion. The controller 114 is adapted for receiving and processing the motion signal and is adapted providing the pain signal as a function of the motion signal and as a function of the corresponding signals. The indicator 116 may be driven by the circuit(s) 110 and/or by the controller 114. In one form, the controller is a processor having a memory device 122 storing computer executable instructions for calculating the pain signal and wherein the processor is adapted to execute the instructions.

In one exemplary optional form, a method for measuring pain of a person is described. The method is for use with the tissue of the person, and comprises:

illuminating the tissue of the person;
sensing light emitted or reflected by the tissue of the person;
generating a light signal indicative of a light parameter of the sensed light;
sensing an electrical parameter of the tissue of the person;
generating an electrode signal indicative of an electrical parameter of the sensed electrical parameter;
sensing a temperature of the tissue of the person;
generating a temperature signal indicative of the sensed temperature;
processing the light signal, the electrode signal and the temperature signal and providing a pain signal which is a function of the processed signals; and
providing an indication which is indicative of the pain signal.

The phrase measuring pain as used in this document is in reference to measuring one or more parameters that are reflective of pain. As doctors will understand, the device does not measure pain per se but measures one or more parameters that are reflective of pain and directly related to a level of pain.

In one exemplary optional form, the motion sensor comprises at least one of an accelerometer; a GPS sensor; and a gyroscope.

In one exemplary optional form, the light source comprises at least one of: a light source emitting light having a frequency in the range of near infrared wavelengths (e.g., about 1014 Hz; about 1000 nm in wavelength); an LED (light emitting diode); an LED emitting visible light; and an LED emitting light having a frequency in the range of infrared wavelengths (e.g., between 1011 to 1015 Hz; between 1000 nm to 1 cm in wavelength).

In one exemplary optional form, the optical sensor comprises at least one of: a photodetector; and a light sensitive element and the light parameters comprise at least one of: light intensity; light frequency; light wavelength; and a light emitting pattern (chirp pattern).

In one exemplary optional form, the surface electrode comprises at least one of: an electrode (e.g., a wet electrode, an AG/AGCL Electrode (Lead), or a dry electrode such as metal probes adapted to contact the tissue); and conductive elements adapted to contact the tissue.

In one exemplary optional form, the electrical parameters comprise at least one of: voltage; current; resistance; capacitance; inductance; impedance; and charge.

In one exemplary optional form, the temperature sensor comprises at least one of: a resistive temperature sensitive element; a bi-metallic element; and a MEMS temperature sensor.

In one exemplary optional form, the one or more circuits comprise: an analog to digital circuit; a signal conditioning circuit; a filtering circuit; and hardware and drivers for optical transceivers in both normal and chirp modulation modes.

In one exemplary optional form, the light source, the optical sensor, the surface electrode, the temperature sensor and the one or more circuits comprise one unitary, integrated component and the controller is a separate, unitary, integrated component and further comprising a wireless link between the controller and the one or more circuits.

In one exemplary optional form, the light source, the optical sensor, the surface electrode, the temperature sensor, the one or more circuits, the power supply and the controller comprise one unitary, integrated component.

In one exemplary optional form, the indicator comprises at least one of: one or more LEDs; an LCD device; a screen;

and a set of LEDs operating in visible wavelength as indicators of hemodynamic change rate and/or pain level.

In one exemplary optional form, the controller comprises a processor having a memory device storing computer executable instructions which estimate hemodynamic parameters and wherein the processor is adapted to execute the instructions.

In one exemplary optional form, the hemodynamic parameters comprise at least one of the following: hemoglobin oxygenation; hemoglobin deoxygenation; heart rate; respiration rate; forehead and/or body temperature; and forehead and/or body impedance.

In one exemplary optional form, the controller comprises a processor having a memory device storing computer executable instructions wherein the processor processes the received, corresponding signals according to at least one of the following: instructions for an algorithm to compute the pain signal based on hemodynamic parameters and hemodynamic response to external and/or internal stimulus in real-time or near real-time; instructions for comparing the signals to a reference (history of hemodynamic parameters and hemodynamic response; and instructions for scaling the hemodynamic response to the range of [0, 10].

In one exemplary optional form, the instructions for the algorithm executed by the processor comprises instructions for fusing over a preset time interval a plurality of samples of a magnitude of the light signal LS, the electrode signal ES, and the temperature signal TS, adjusted by preset weights a, b, and c, to compute a pain indicative signal PS corresponding to a fused signal according to the following:

Fused Signal=$\Sigma(a*LS+b*ES+c*TS)$.

In another exemplary optional form, the instructions for the algorithm executed by the processor comprises instructions for using over a preset time interval a plurality of samples of a magnitude of a light pain signal LPS indicative of a pain level, an electrode pain signal EPS indicative of a pain level, and a temperature pain signal TPS indicative of a pain level, adjusted by preset weights a, b, and c, to compute an estimated pain indicative signal PS corresponding to a fused signal according to the following:

Fused Signal=$\Sigma(a*LPS+b*EPS+c*TPS)$.

In one exemplary optional form, the instructions for the algorithm executed by the processor comprises instructions for summing over a preset time interval of a plurality of samples of a magnitude of the light signal LS, the electrode signal ES and the temperature signal TS, and/or related parameters, as noted in the Appendix.

In one exemplary optional form, the instructions for the algorithm executed by the processor comprises instructions for summing over a preset time interval of a plurality of samples of a magnitude of the light signal LS, the electrode signal ES and the temperature signal TS, wherein each sample is compared to preset ranges and the magnitude of the signals is adjusted according to a relationship between each signal and the preset ranges.

In one exemplary optional form, the instructions comprise instructions for inputting personal input into the controller by an input device such as a keypad or keyboard, the personal input including conditions and/or environments of the person and wherein the pain signal is coordinated with the personal input whereby improved person pain management is provided.

In one exemplary optional form, the personal input includes a level of consciousness indicator, such as:

0 Awake;
2 Light/Moderate Sedation;
4 General Anesthesia;
6 Deep Hypnotic State;
8 Burst Suppression; and
10 Fully unconscious.

In one exemplary optional form, the controller processes at least one of the corresponding signals according to chirp based optical modulation.

In one exemplary optional form, the optical sensor comprises a blood oxygenation sensor for sensing a blood oxygenation of the person and wherein the chirp based optical modulation by the processor comprises measuring the light signal in different wavelengths as indicative of blood oxygenation.

In one exemplary optional form, the chirp based optical modulation comprises varying a carrier frequency in optical modulation over time to mimic hemodynamic response in different wavelengths over time to detect hemodynamic response recursively over time in a serial (recursive) approach.

In one exemplary optional form, the controller calculates respirations and heart rate by evaluating different frequency components in raw sensor data from the optical sensor.

In one exemplary optional form, a respiratory signal has a frequency component of the raw data [2-5 Hz] which can be extracted using a band pass frequency with cut off [2-5 Hz], and wherein the processor evaluates frequency components of 5-100 Hz to obtain heart rate.

In one exemplary optional form, the controller comprises a processor having a memory device storing computer executable instructions comprising machine learning techniques and wherein the processor is adapted to execute the instructions, wherein the machine learning techniques include at least one of: adaptive and non-adaptive noise cancelation of noise in the signals; signal Envelope Detection; low pass, band-pass, band-stop and high pass digital filters to extract different hemodynamic parameters from sensor data spectrum; and supervised or unsupervised clustering including at least one of k-means, fuzzy c-means artificial neural networks, support vector machine, fuzzy systems to characterize hemodynamic response across different persons (persons) and across days (inter and intra subject variability characterization).

In one exemplary optional form, the controller calibrates the system using a baseline wander correction algorithm based on at least one of adaptive or non-adaptive filtering.

In one exemplary optional form, data is provided to the controller indicative of feedback from a person to train the controller or set a range.

In one exemplary optional form, the data comprises subjective pain measurements from the person synchronized with pain indicator measurements by the system, wherein the subjective pain measurement comprise:

0-1 No pain;
2-3 Mild pain;
4-5 Discomforting—moderate pain;
6-7 Distressing—severe pain;
8-9 Intense—very severe pain;
10 Unbearable pain.

In one exemplary optional form, the controller synchronizes objective hemodynamic parameters of the sensor signals with subjective measurements provided by the person so that the sensor and person or a physician establishes communication and coordination between the sensors and the person or physician.

In one exemplary optional form, the controller generates commands to which the person responds to at a particular point to define a baseline. For example, the device will continuously or at programmed intervals ask the person to respond to the device by defining his subjective pain level through a mobile phone or other communication interface. As a result, the device/system is capable of calibrating/coordinating its objective measurements with the person's subjective measurements. This process will also help with baseline creation so that the objective and subjective pain levels correlate at the moment in time.

In one exemplary optional form, the controller is responsive to a person or physician to trigger the hemodynamic monitor to make measurements and define a baseline.

In one exemplary optional form, a person indicates his/her pain status among environmental parameters to train the device for threshold definition.

In one exemplary optional form, the device communicates with the persons regarding its pain status in order to define a baseline and threshold for device training and personalization.

In one exemplary optional form, the system is configured to be implantable within a person. One device variation could be a single patch placed on the person forehead, head, or neck. Another optional variation could be multiple sensors being placed on the forehead or circumference of the head similar to a bandana. Yet another optional variation of the device and method could be an implantable device with sensors and battery and wireless operation that can be continuous or activated by mobile phone or any other activator to activate the sensor for a programmed period of time and transmit information to the receiver outside or inside the body. The implantable device could be rechargeable over the scalp. This implantable device could be implanted underneath hair in or underneath the scalp via a simple insertion like a hairpin or incision. The implantable device will be removable as well. Implantable device could have flat or other geometrical form factors to fit the person's head/scalp/skull. The receiver device could be a mobile phone, a hat, headband, or other similar form factors. The implantable device could be powered using an external power source such as an RF generator or coil-to-coil power generation where a capacitor in the device stores enough energy to perform a required measurement and transmission of the information.

Figure 2:
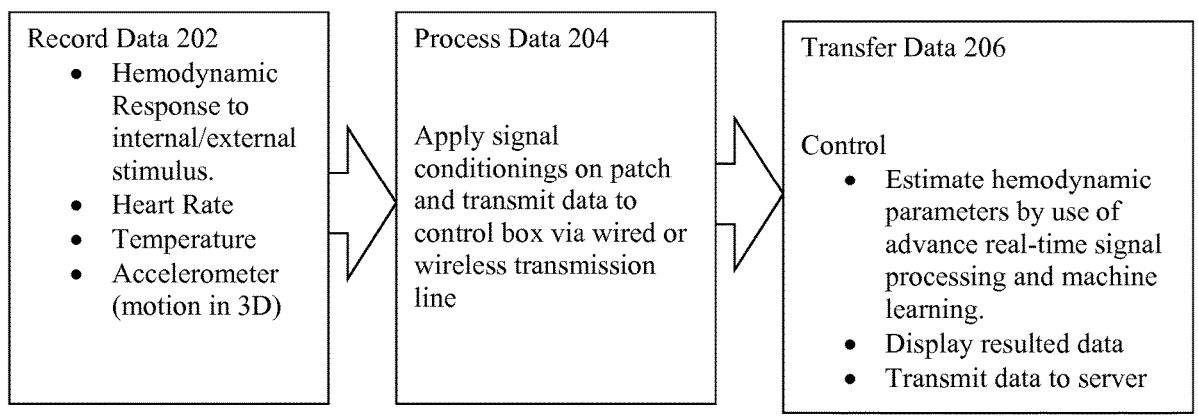
FIG. 2 illustrates a block diagram of the device for the real-time tracking of the cerebral hemodynamic changes on ambulatory subjects using the Real-time Tracking of Cerebral Hemodynamic Response (RTCHR) system.

In further detail, referring to FIG. 2, the Real-Time Tracking of Cerebral Hemodynamic Response (RTCHR) system 100 includes three stages. A first stage 202 employs a sensor unit for recording data. The sensor unit includes, for example, a surface electrode and optical sender/receiver LEDs, an accelerometer, a GPS, and temperature sensors. The sensor data are processed and properly conditioned in the next stage 204 and then, with a wired or wireless transmission unit, the sensor data are transferred at a third state 206 to a control for further processing (e.g., advance real-time signal processing and machine learning) to estimate hemodynamic response changes due to external/internal stimulus (anesthesia, pain, and the like), heart rate, respiration and other parameters. The advance real-time signal processing stage includes real-time denoising, baseline wander removal, extraction of different band of sensor data related to heart pulse, respiration and/or cerebral hemodynamic response trace based on frequency domain filtering envelop detection and real-time source separations. To estimate hemodynamic response change over time some statistical and morphological features such as norm, root-mean-square, skewness, kurtosis, entropy, and the like are extracted and input to a real-time machine learning stage to compare blood oxygen consumption pattern between present and past. Also, machine learning based predictive models can be used to predict onset of pain in the close future in pain management applications.

Figure 3A:
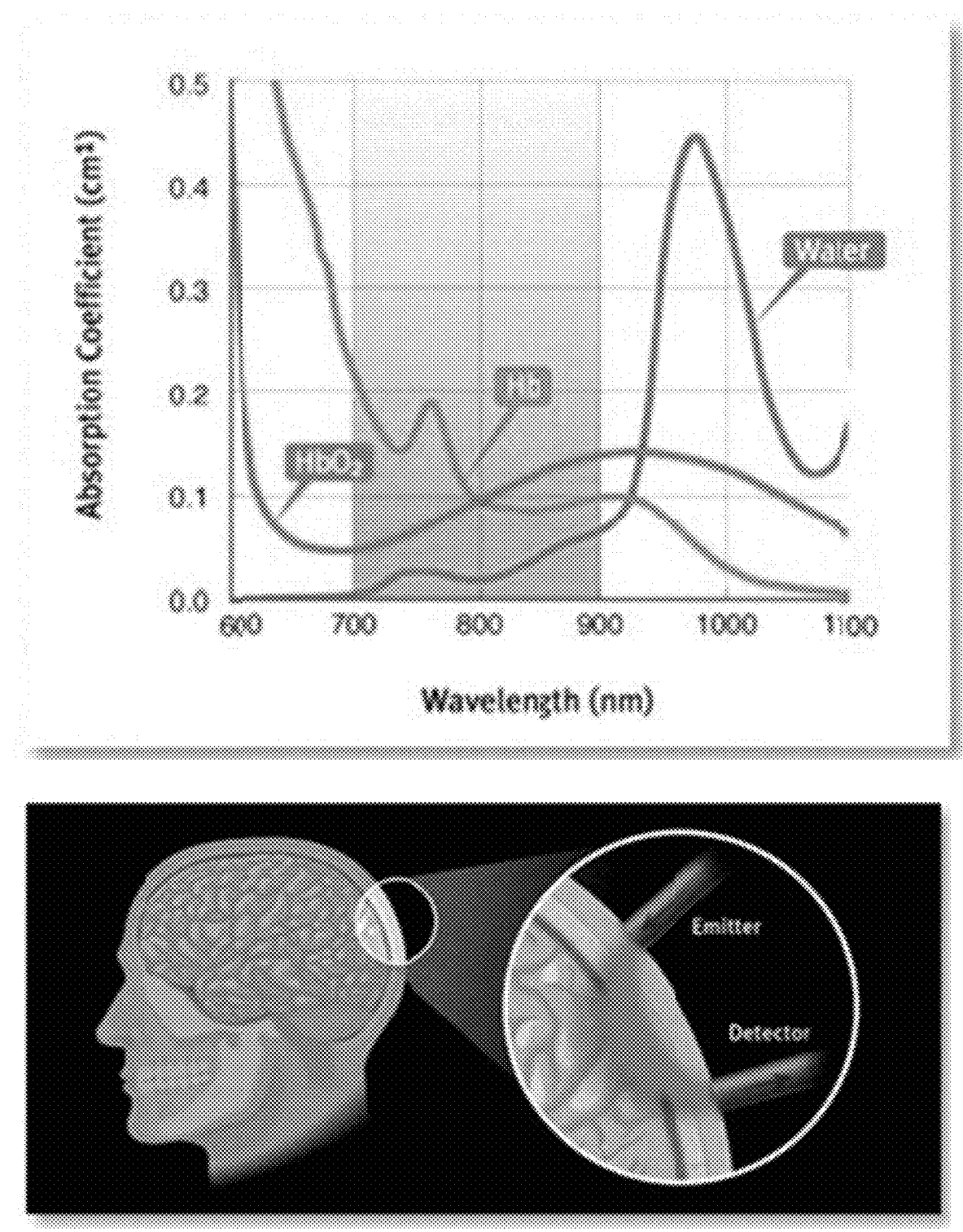
FIGS. 3A and 3B illustrate the physics of chirp optical modulation to track hemodynamic response changes.
Figure 3B:
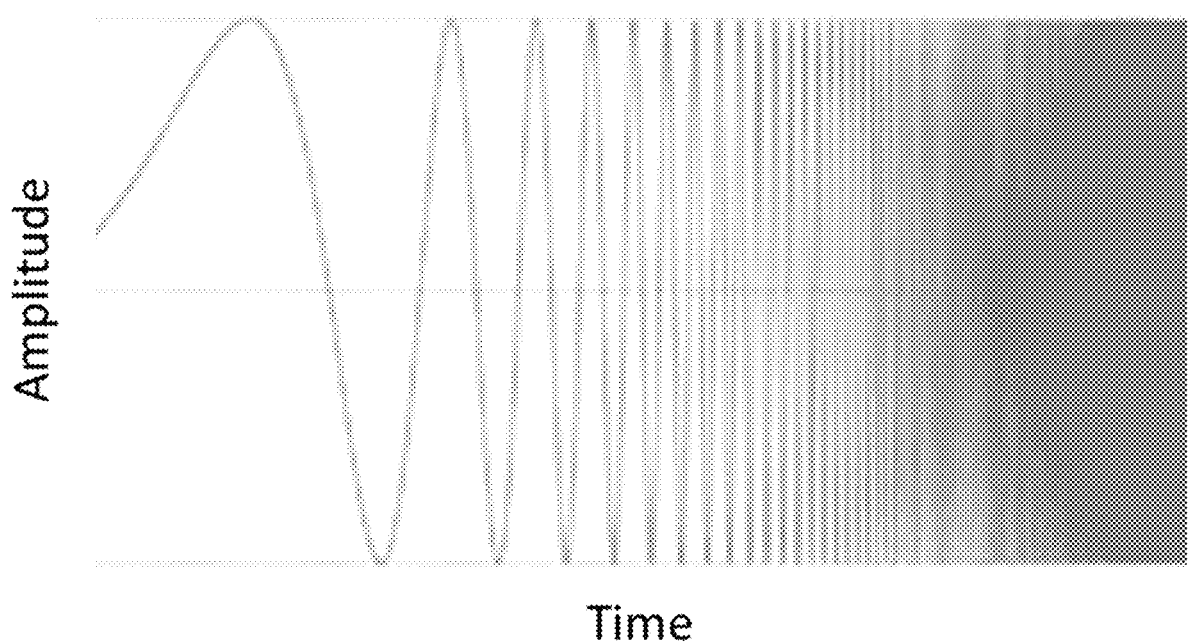

The advantage of the current invention as compared to other digital interfaces is that in one embodiment of the invention a single forehead patch can be used to estimate hemodynamic parameters using a new optical modulation which makes it different compared to current optical sensing such as oximetry and functional near-infrared (fNIR) technology devices, such as shown in FIG. 3A. FIG. 3A illustrates on the left a graph of the absorption of spectra of oxy-Hb and deoxy-Hb in the near infrared range (the three graphical lines illustrate HbO2, Hb, and water, from left to right). FIG. 3A on the right illustrates the path of light on a human head from emitter to detector. A chirp signal such as illustrated in FIG. 3B is used to emit light with different wavelengths in red and near infra-red ranges. By use of chirp modulation according to the invention, tracking of hemodynamic response changes will be maximized and RTCHR provides a new class of optical sensing compared to oximetry and spectroscopy.

Chirp based optical modulation according to one aspect of the invention measures blood oxygenation in different wavelengths. In chirp modulation, a carrier frequency in optical modulation varies over time to mimic hemodynamic response in different wavelengths over time. In contrast, in oximetry, only two wavelengths are used and in NIR spectroscopy a set of optical senders and receivers are used to get hemodynamic responses over different wavelengths in parallel. Chirp based optical modulation according to one aspect of the invention detects hemodynamic response recursively over time. Since hemodynamic response is slow, the system detects hemodynamic responses over different wavelengths in a serial (recursive) approach. Modulation pattern and number and range of frequency (wavelength) modulation can be controlled by a person at software level, but hardware for chirp modulation may also be used to implement control. For instance, a person could take two wavelengths readings, one in red field and another in near-infra red. On this case, the device acts as a pulse oximeter. In other words, the system with its novel recursive modulation ability can induce any pattern including two wavelength readings (oximeter mode) or chirp mode (multiple wavelengths reading).

It is noteworthy that the single forehead patch could include several of the hemodynamic and other sensors for multiple measurements across different locations on the forehead or the brain.

A typical application for RTCHR system 100 and method according to the invention provide objective pain level assessment. Currently in clinics, persons are asked to score their pain level to a number between 0-10: 1-3: mild pain, 4-7 moderate pain and 8-10 sever pain. The system 100 and its method are capable of estimating pain level by tracking hemodynamic baselines and/or changes in response to internal/external pain stimulus. For example, in one embodiment, previous sensor readings from few minutes and/or hours ago are used as baseline hemodynamic response and the current sensor reading is compared with the history of data to determine level of deviation. Alternatively and in addition, a baseline could be arbitrary. If a nurse, doctor, or the person starts baseline recording at a certain point in time or under certain conditions, this also could be considered baseline. The device/system will allow a person (e.g., person, doctor, technician) to choose and set up a certain condition as "baseline". Yet, when an infant cries or is in stress due to pain, the higher level or threshold could be considered baseline, too, not necessarily the lowest measurement. Thus, a baseline is a reference, either arbitrary or defined.

In general, a baseline is a reference point. For example, a baseline may be established in several ways. 1) When the subject is in a normal state or in pain. In a normal state, any increase in pain is tracked; in a pain state, increases or decrease in pain due to therapy are tracked. 2) In a situation where there is previous data from a person, the data may be used to establish a baseline, such as body temperature or blood pressure. For example, one day data could be used to establish a normal range of body temperature.

Figure 4:
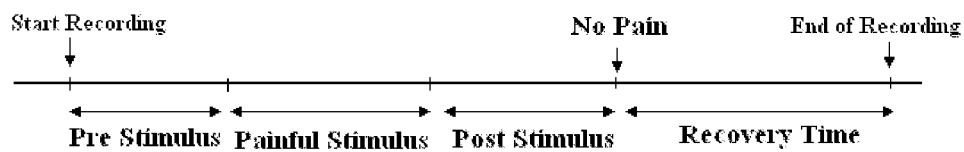
FIG. 4 illustrates the period of time during which the assessments of FIGS. 5-8 were taken.

To demonstrate the ability of RTCHR to estimate pain levels, subject data using the forehead patch as shown in FIG. 1, before, during and after an external pain stimulus (e.g., sever cold, heat and sharp pains) were recorded. FIGS. 5-8 illustrate the recorded data, showing the hemodynamic changes in response to external and internal pain stimulus. The Y-axis is an estimated pain level (1st norm scaled to 0-10) per second for first and second subplots and per 10 second for the third subplot. FIG. 4 illustrates the period of time during which the assessments of FIGS. 5-8 were taken.

Figure 5:
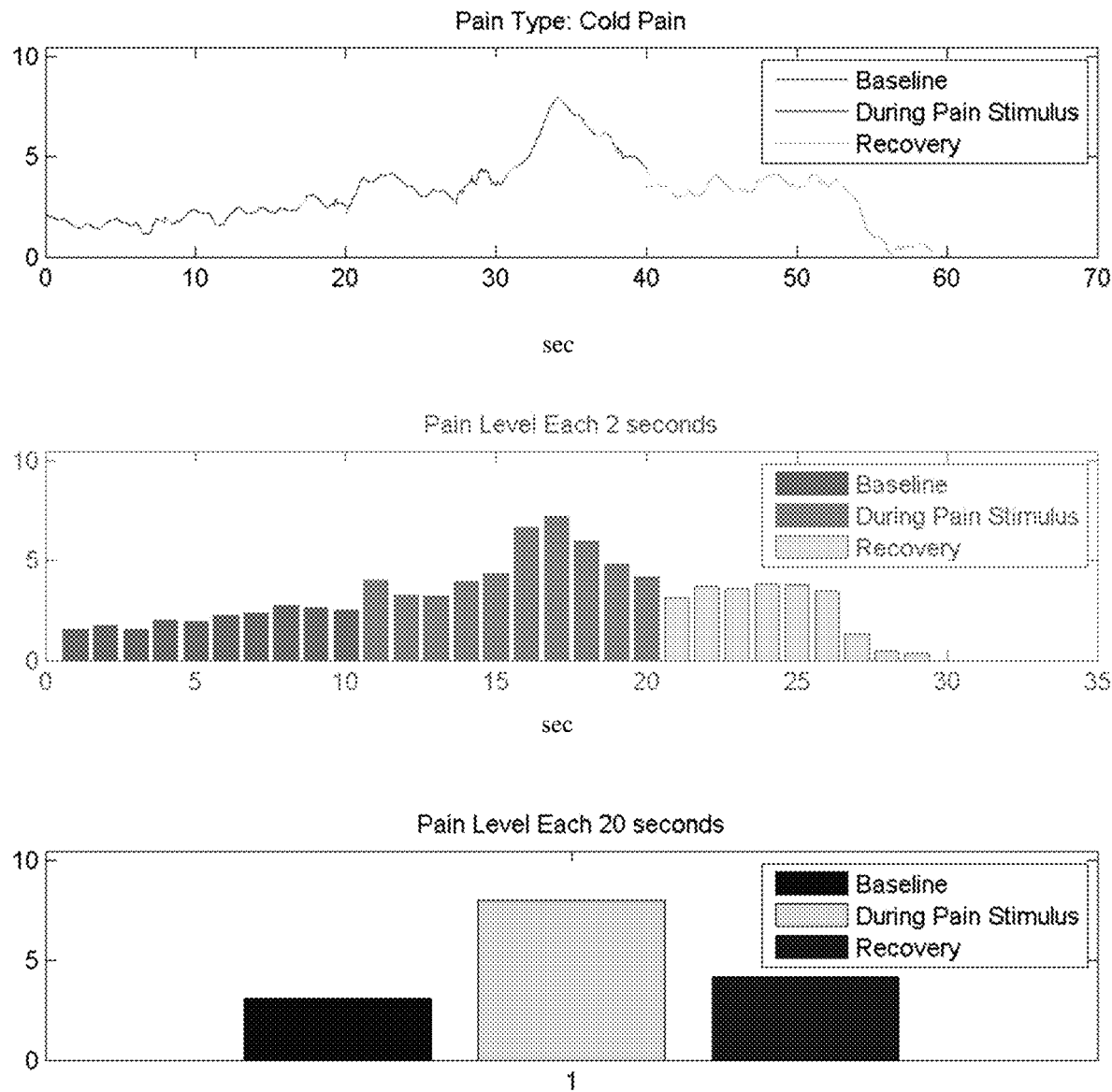
FIG. 5 illustrates graphs of Objective Pain Level Assessment: hemodynamic changes in response to external severe cold pain stimuli.

FIG. 5 illustrates graphs of Objective Pain Level Assessment: hemodynamic changes in response to external severe cold pain stimuli. Levels 1-10 during the first 20 seconds illustrate the baseline. Levels 11-20 during the next 20 seconds illustrate the response during pain stimulus. Levels 21-30 during the last 20 seconds illustrate the response during recovery after pain stimulus has ended.

Figure 6:
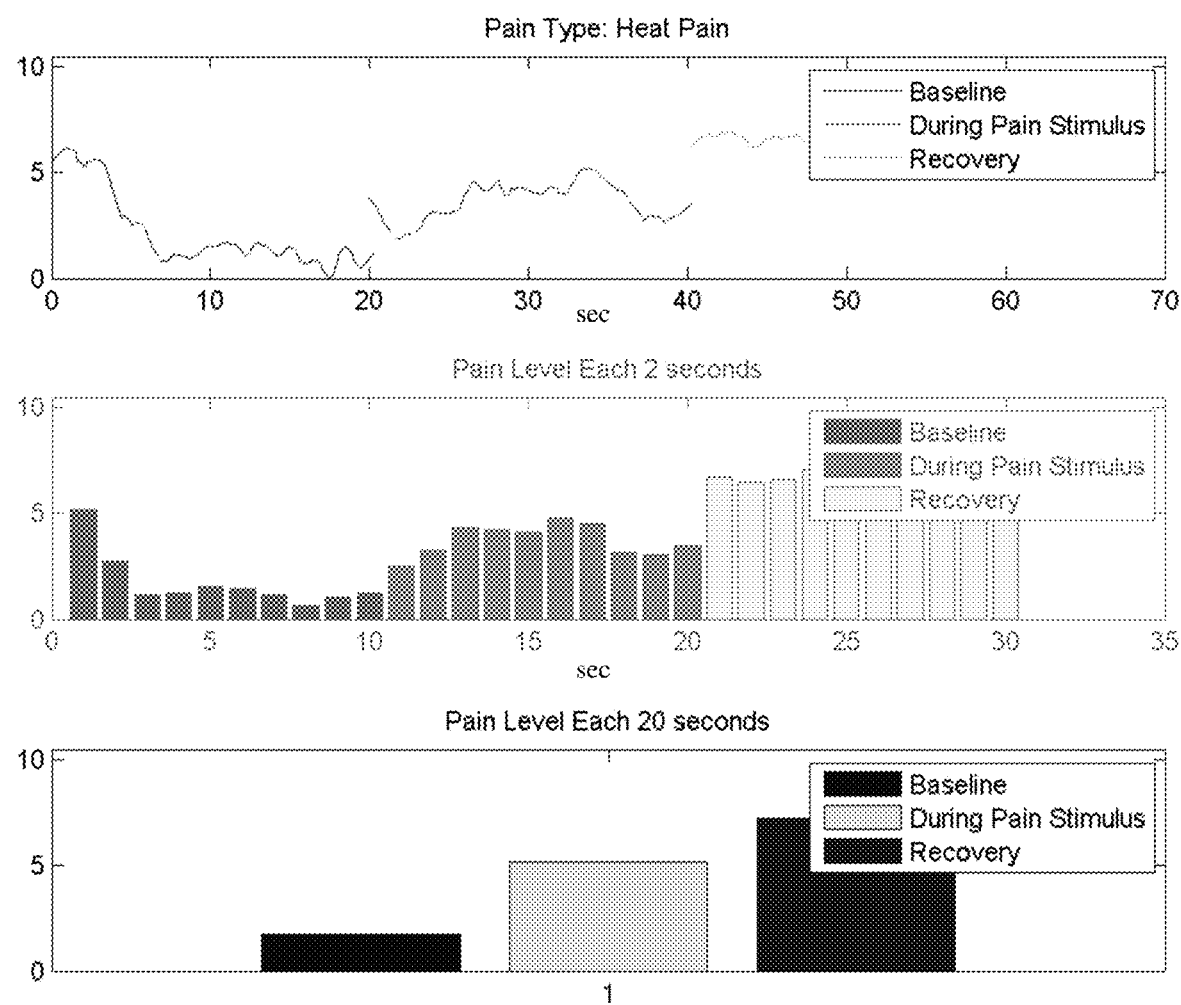
FIG. 6 illustrates graphs of Objective Pain Level Assessment: hemodynamic changes in response to external severe heat pain stimuli. Hemodynamic response did not return to baseline due to continued burning sensation.

FIG. 6 illustrates graphs of Objective Pain Level Assessment: hemodynamic changes in response to external severe heat pain stimuli. Hemodynamic response did not return to baseline due to continued burning sensation. Levels 1-10 during the first 20 seconds illustrate the baseline. Levels 11-20 during the next 20 seconds illustrate the response during pain stimulus. Levels 21-30 during the last 20 seconds illustrate the response during recovery after pain stimulus has ended.

Figure 7:
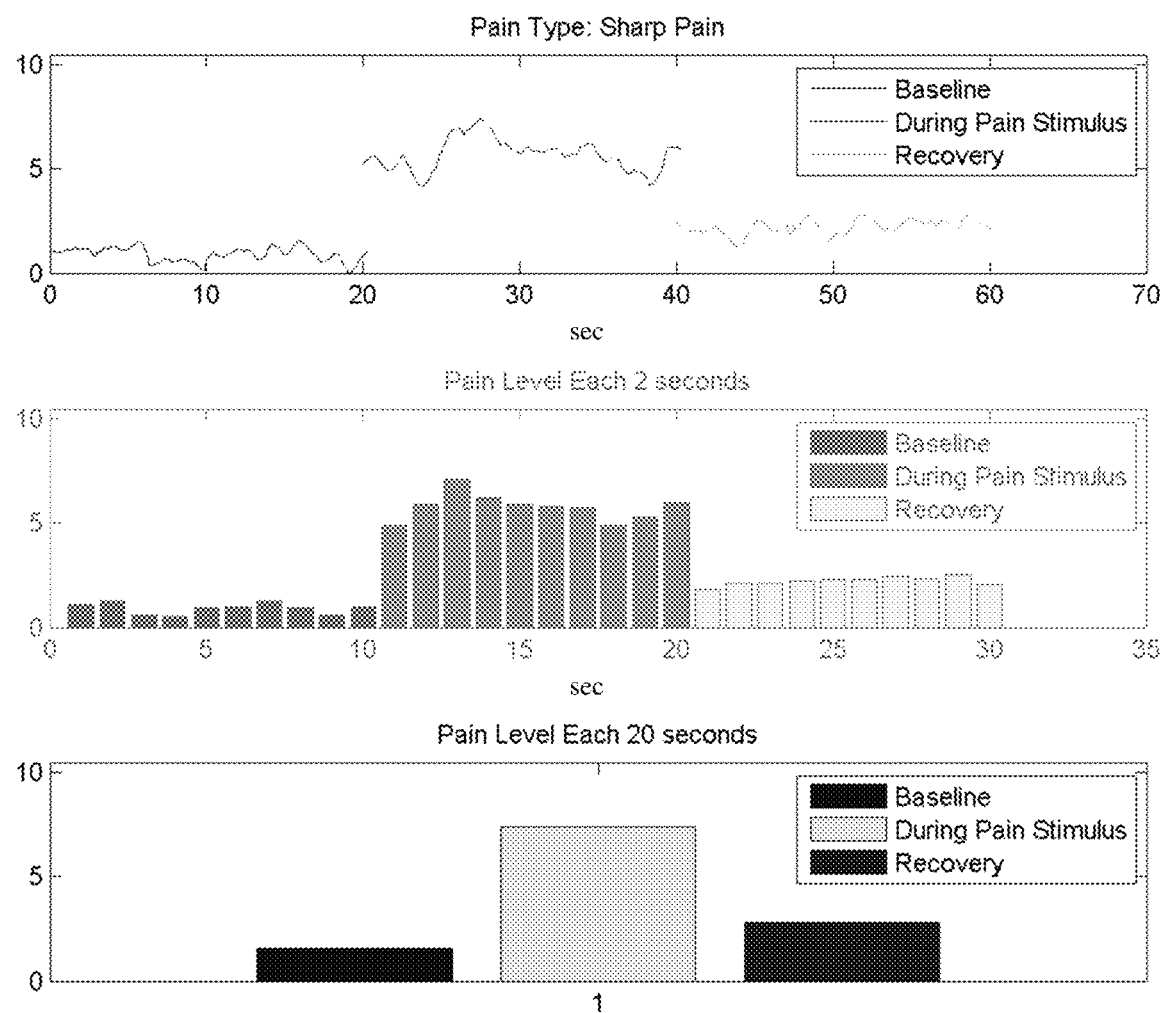
FIG. 7 illustrates graphs of Objective Pain Level Assessment: hemodynamic changes in response to external severe sharp pain stimuli.

FIG. 7 illustrates graphs of Objective Pain Level Assessment: hemodynamic changes in response to external severe sharp pain stimuli. Levels 1-10 during the first 20 seconds illustrate the baseline. Levels 11-20 during the next 20 seconds illustrate the response during pain stimulus. Levels 21-30 during the last 20 seconds illustrate the response during recovery after pain stimulus has ended.

Figure 8:
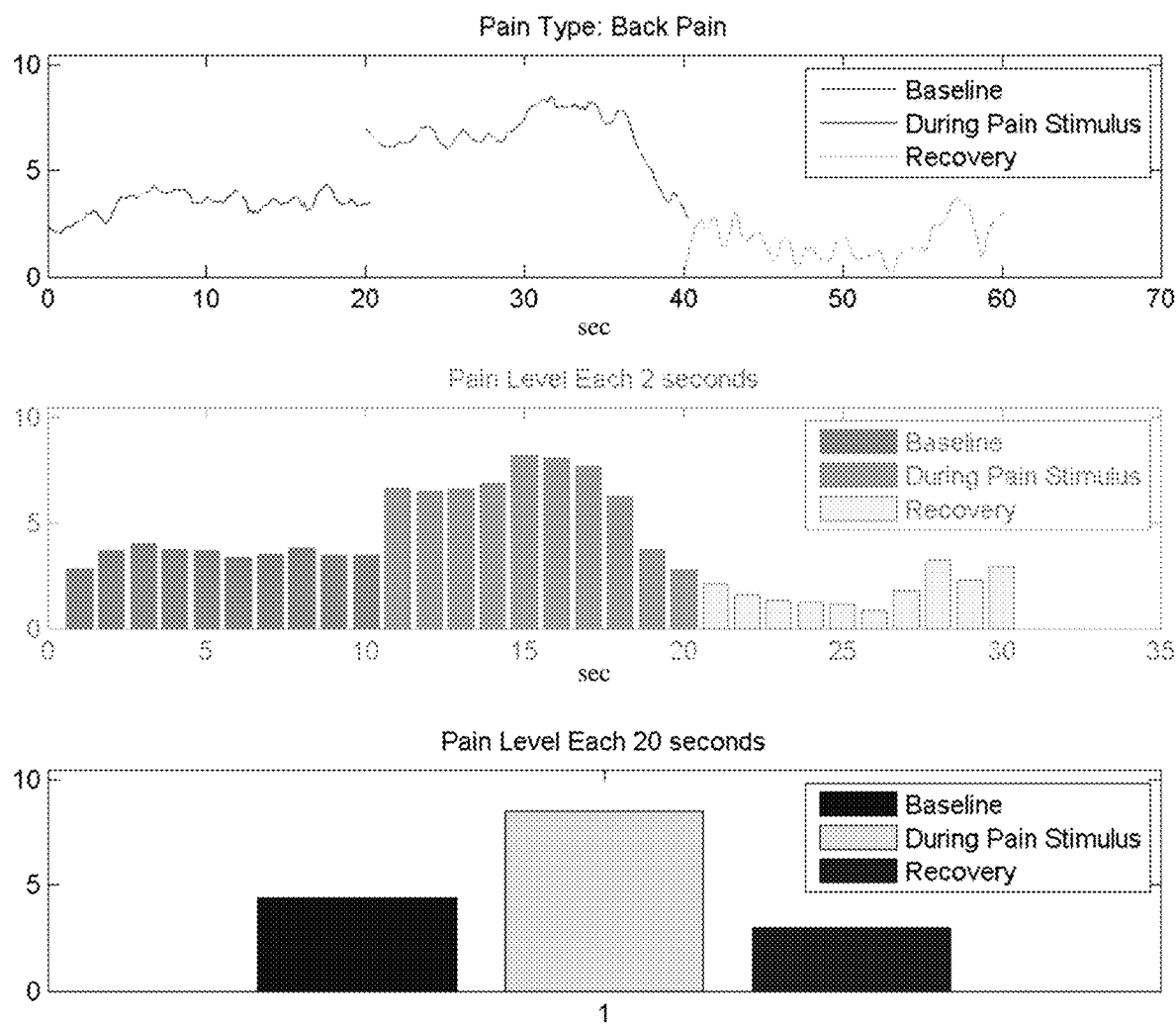
FIG. 8 illustrates graphs of Objective Pain Level Assessment: hemodynamic changes in response to internal severe back pain stimuli. Subject with back pain was asked to twist his back to temporarily increase pain level.

FIG. 8 illustrates graphs of Objective Pain Level Assessment: hemodynamic changes in response to internal severe back pain stimuli. Subject with back pain was asked to twist his back to temporarily increase pain level. Levels 1-10 during the first 20 seconds illustrate the baseline. Levels 11-20 during the next 20 seconds illustrate the response during pain stimulus. Levels 21-30 during the last 20 seconds illustrate the response during recovery after pain stimulus has ended.

Figure 9:
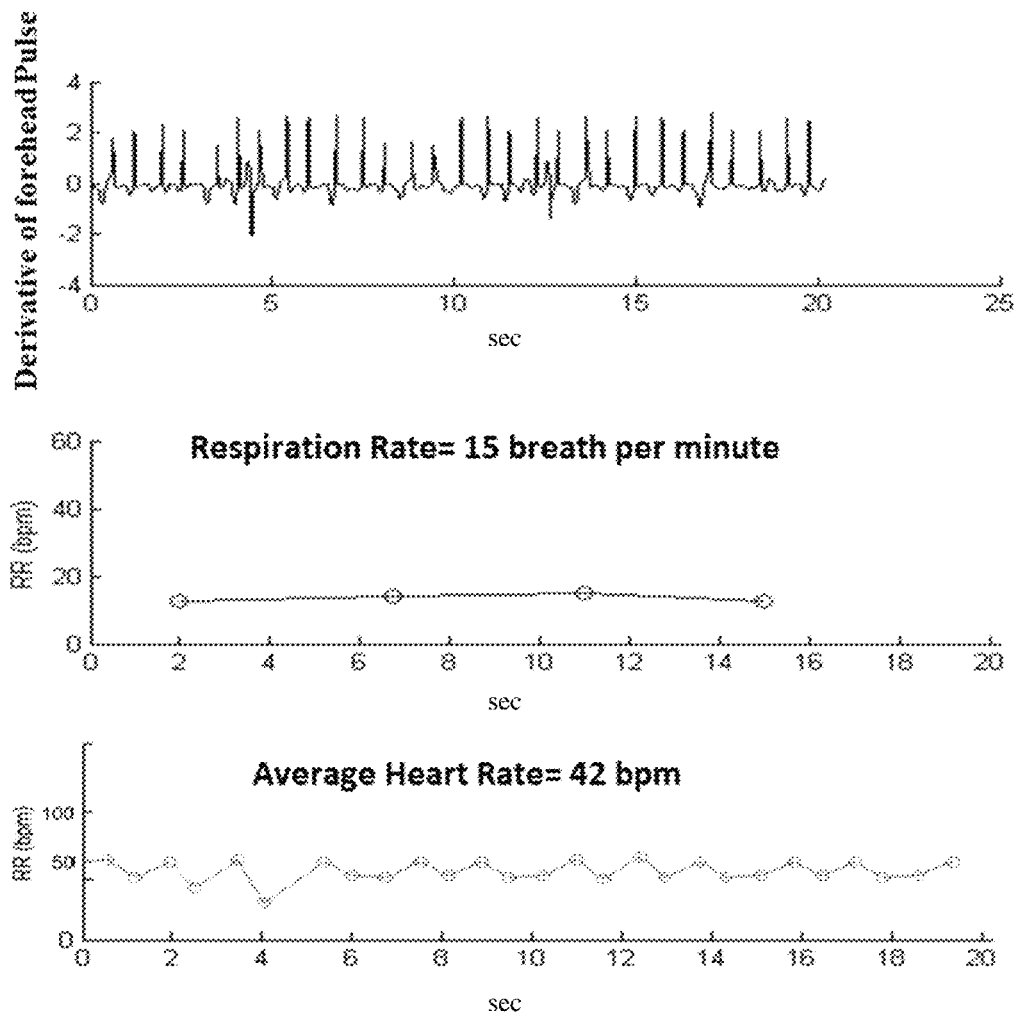
FIG. 9 illustrates graphs of heart and respiration rate Estimation: The derivative of forehead pulse can be used to estimate Heart and respiration rates.

The RTCHR system 100 and its method also provide heart and respiration rates. FIG. 9 illustrates graphs of heart and respiration rate Estimation: The derivative of forehead pulse can be used to estimate Heart and respiration rates. FIG. 9 shows a typical forehead pulse and estimated heart and respiration rates. To calculate respiration and heart rate, the processor evaluates different frequency components in raw sensor data from the optical sensor. A respiratory signal is a frequency component of the raw data [2-5 Hz] which can be extracted using a band pass frequency with cut off [2-5 Hz]. To get heart rate, the processor evaluates frequency components of 5-100 Hz.

Heart rate and/or respiration rate can be measured or calculated manually or automatically. In one embodiment, respiration rate and heart rate signals can be extracted from a light signal and/or surface electrode signal and for analysis according to at least some embodiments of the systems and methods of the invention.

Another application for RTCHR is in the area of sensation as associated with brain activity. Images in movies and photos can generate empathic pain. Subjects shown a series of images or movies with injuries or other pain related events have reported definite pain to at least one image of movie. It has been determined that subjects who report pain in response to such images activate pain matrix regions in the brain, which are responsible for generating pain. Therefore, observing painful images modulates motor responses, which suggest sensorimotor involvement. For example, a person reported feeling physical pain when observing his wife experience superficial pain. Various types of pain have been measured, for instance, somatic pain (e.g., tingling, aching, sharp, shooting, throbbing, sickening, splitting, heavy, stabbing, and tender types of pain have been described) and visceral pain. Further, rCBF response to heighted unpleasantness has been recorded. Pain activates a large amount of neural tissue. However, understanding chronic pain is unresolved. Imaging studies have illustrated that chronic pain is associated with functional, structural and chemical changes in the brain; however, it is not known how neural activity is translated into a feeling. Areas of the brain that are usually active provide for pain inhibition, and a lack of pain inhibition causes chronic pain. In addition, dysfunctional psychological processing changes underlying patterns of brain activation and causes chronic pain. Typically, pain is reported by asking subjective questions of persons and not by imaging anatomic information and determining the activation of brain distress centers. RTCHR may be used to better evaluate and understand these aspects.

Studies have been made using a functional Magnetic Resonance Imaging ("fMRI") scanner to study pain. The fMRI records the variable magnetic property of tissue. For instance, fMRI scanning has been utilized during the presentation of real noxious heat stimuli, as well as during the suggestion of a real noxious heat stimuli to a set of eight subjects. All the subjects reported a sensation of at least heat during the suggestion and five reported pain. In addition, fMRI can determine the Blood Oxygen Level Dependent (BOLD) signal, which measures an "effect parameter". However, a disadvantage of using BOLD is that the signal changes are small making the analysis difficult, tedious and complicated, requiring significant subjectivity. RTCHR may be used to better evaluate and understand these aspects.

fMRI has been used to study empathetic pain. For instance, ten pain responders and ten non-responders acting as controls were give a set of pain images and a set of emotional images. Using fMRI the anterior midcingulate cortex ("aMCC") was monitored. The responders consistently activated aMCC, anterior insula, prefrontal cortex and primary (51) and secondary (S2) somatosensory cortex for all pain images and emotional images. In contrast, the non-responders consistently activated aMCC and prefrontal cortex but failed to activate insula, Si or S2. Therefore, regional activation is specifically and actively involved in the generation of pain, and empathetic pain appears to involve the same mechanism. For example, using hypnosis one can direct generation of pain via the usual pain neuromatrix. Once again, RTCHR may be used to better evaluate and understand these aspects. Instead of using fMRI, applying RTCHR provides objective measurements hemodynamic response, heart and respiration rates, to determine and predict the onset of pain.

It is known that brain lesions can cause pain. In addition, it is known that newborns have an exaggerated sensitivity to touch that diminishes with maturity. Further, it has been determined that blocking descending inhibition in animals causes hyperalgesia. Thus it is possible that functional pain is caused by a disruption to descending inhibition. fMRI has also been used to study offset analgesia. Offset analgesia is the perception of profound analgesia during a slight incremental decrease of a noxious heat stimulus that is more pronounced than would be predicted by the rate of the temperature decrease. Offset analgesia is an active process probably involving descending inhibitory mechanisms to modulate pain. Using fMRI, twelve control subjects, free of neurological disorder and chronic pain, completed an offset analgesia procedure. They completed the offset procedure six times; twice at each temperature (high, medium, and low). The results indicated that: 1) during baseline, there is little pain and little activation; 2) during constant, there is pain and plenty of pain activation; and 3) during offset there is less pain and little activation. Therefore, one can conclude that normal controls can be induced to feel pain without any physically noxious stimulus. Functional pain person might generate pain in a similar fashion. Also, normal controls can be induced to feel a noxious stimulus as less painful without any physical change in the stimulus. Therefore, functional pain persons may lack endogenous analgesic mechanisms such as offset analgesia. RTCHR may be used to better evaluate and understand these aspects.

It is possible to utilize a device of the invention to measure issues with brain development in neonates. Some neonates have problems with normal development of the brain and the device is helpful to detect and report such issues despite whether the neonate feels pain or not. For example, a "normal" level of sensor measurement expected in a larger group of neonates (expected baseline data) can be used as a baseline to compare to other neonates who have severe deviation from the baseline. In addition, the device may be used for cerebral monitoring such as a particular brain function monitoring instead of the pain application. For example, the device in at least certain persons may indicate or detect early onset of epilepsy or another brain related issues (e.g., Alzheimer, Parkinson's, brain tumors). Thus, the device may be used to capture early onset of epilepsy or another brain related issues in an inexpensive and ambulatory way by use of a single patch on a forehead or a person or at other locations on the body. In this context, the pain signal comprises a cerebral monitoring signal.

It is also contemplated that the device may be used by athletes for performance enhancement as it relates to cerebral flow and pain perception.

Feedback

In one aspect, feedback from the person may be used to train the system 100 or set a range. Also, a person may choose which days/time should be compared with current time [reference point and baseline setting]. Also, a person's subjective pain level can be compared with objective (automated) pain assessment. This is called interactive pain. Enabled with artificial intelligence and real-time learning mode, this applies self-tuning, particularly when there is a large difference between objective and subject pain levels.

Oximeter/Device Combination

In one embodiment, a pulse oximeter can be modified to also provide a cerebral hemodynamic tracking system according to the invention to measure pain, trauma, epilepsy, level of consciousness, attention monitoring and other brain related applications. For example, the pulse oximeter is modified to detect a light signal, an electrical parameter electrode signal and a temperature signal. In addition, the firmware of pulse oximeter is updated to have access to raw data from LEDs and apply an algorithm for generating a pain signal which is a function of the corresponding signals and for providing an indicator indicative of the pain signal.

Calibration

In one form, baseline wander correction algorithms (based on adaptive or non-adaptive filtering techniques) may be used to perform self-calibration and to account for sensor data drift coming from hardware and/or human condition changes such as sweating or motion.

Another application of at least some embodiments of the device or method of the invention is in various product configurations for the OBGYN applications. For example, a consumer patch and a smart phone app could be used to track uterus contractions prior to childbirth. In today's environment, expectant mothers have to record the frequency of the uterus contractions and keep a record with a timer in hand. Once contractions happen too closely, it will be time to attend a clinic or hospital for child delivery. So often expectant mothers miss the true contraction frequency and associated pain level. Uterus contractions cause proportional pain. At least some embodiments of the device or method of the invention attached to the forehead could keep track of the pain associated with the uterus contractions and maintain a concise time and pain amplitude profile without a subject's intervention. As a result, at least some embodiments of the device or method of the invention could advise the subject when to attend to the clinic while simultaneously transmitting the complete contraction profile to the clinic or the attending doctors prior to arrival.

At least some embodiments of the device or method of the invention could be used for epidural pain management to measure pain and automatically administer pain medication.

At least some embodiments of the device or method of the invention could be used for post childbirth pain management in natural or C-section type childbirth where pain management is a major issue. All data collected can be integrated into a patient profile at the hospital EMR.

Yet another application could be a handheld device for tracking children pain due to teething or other painful situations to assist parents in managing children or infant pain. At least some embodiments of the device or method of the invention could be similar to a handheld thermometer with memory. Routine baseline measurements can be recorded. Once the infant is in a stressful situation and crying for no apparent reason, parents can place the device on the forehead for a period of time to measure if pain is present. At least some embodiments of the device or method of the invention could be used on neonates at the hospitals or non-responders in ICU and nursing homes.

Yet another application is in post-surgery where a patient's pain is being managed by a PCA (patient controlled analgesia) infusion pump. Many post-surgery cases involve keeping a patient at a hospital for 3-7 days, connected to a PCA pump where the patient controls the amount of pain medication delivery. While this is very efficient compared to a preset infusion rate, in many situations when a patient falls sleep for 8-12 hours, the lack of pain management leads to adverse events such as inflammation or other causes of chronic pain. In these situations, if the acute pain is not treated properly, it can translate to chronic pain which is inconvenient to the patient and costly the healthcare system.

At least some embodiments of the device or method of the invention could be programmed to either administer a drug by instructing the infusion to deliver more medication, wake the patient up by sound or other stimulus, or send a notification to the nursing station. Therefore, pain is managed continuously even when patients are sleep. All data from the device will be integrated into the hospital EMR.

Yet another application is in pain medication drug discovery. Pain medication drug discovery today is a cumbersome process. During clinical trials, a patient is asked for a subjective pain level in order to learn if the drug is effective. So often this type of drug discovery leads to failure due to a placebo effect or improper subjective pain level reporting. Utilizing at least some embodiments of the device or method of the invention, a majority of the ambiguity in pain drug discoveries could be resolved. Companies also can receive real-time effect of their newly developed pain medications from subjects and patients enrolled in clinical trials in real-time.

Yet another variation of At least some embodiments of the device or method of the invention could be to identify and diagnose other neurological disorders such as onset or prediction of bipolar disorder, mood change, schizophrenia, and/or depressions.

The Abstract and summary are provided to help the reader quickly ascertain the nature of the technical disclosure. They are submitted with the understanding that they will not be used to interpret or limit the scope or meaning of the claims. The summary is provided to introduce a selection of concepts in simplified form that are further described in the Detailed Description. The summary is not intended to identify key features or essential features of the claimed subject matter, nor is it intended to be used as an aid in determining the claimed subject matter.

For purposes of illustration, programs and other executable program components, such as the operating system, are illustrated herein as discrete blocks. It is recognized, however, that such programs and components reside at various times in different storage components of a computing device, and are executed by a data processor(s) of the device.

Although described in connection with an exemplary computing system environment, embodiments of the aspects of the invention are operational with numerous other general purpose or special purpose computing system environments or configurations. The computing system environment is not intended to suggest any limitation as to the scope of use or functionality of any aspect of the invention. Moreover, the computing system environment should not be interpreted as having any dependency or requirement relating to any one or combination of components illustrated in the exemplary operating environment. Examples of well-known computing systems, environments, and/or configurations that may be suitable for use with aspects of the invention include, but are not limited to, personal computers, server computers, handheld or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the aspects of the invention may be described in the general context of data and/or processor-executable instructions, such as program modules, stored one or more tangible, non-transitory storage media and executed by one or more processors or other devices. Generally, program modules include, but are not limited to, routines, programs, objects, components, and data structures that perform particular tasks or implement particular abstract data types. Aspects of the invention may also be practiced in distributed computing environments where tasks are performed by remote processing devices that are linked through a communications network. In a distributed computing environment, program modules may be located in both local and remote storage media including memory storage devices.

In operation, processors, computers and/or servers may execute the processor-executable instructions (e.g., software, firmware, and/or hardware) such as those illustrated herein to implement aspects of the invention.

Embodiments of the aspects of the invention may be implemented with processor-executable instructions. The processor-executable instructions may be organized into one or more processor-executable components or modules on a tangible processor readable storage medium. Aspects of the invention may be implemented with any number and organization of such components or modules. For example, aspects of the invention are not limited to the specific processor-executable instructions or the specific components or modules illustrated in the figures and described herein. Other embodiments of the aspects of the invention may include different processor-executable instructions or components having more or less functionality than illustrated and described herein.

The order of execution or performance of the operations in embodiments of the aspects of the invention illustrated and described herein is not essential, unless otherwise specified. That is, the operations may be performed in any order, unless otherwise specified, and embodiments of the aspects of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the aspects of the invention are achieved and other advantageous results attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the aspects of the invention by way of example and not by way of limitation. This description enables one skilled in the art to make and use the aspects of the invention, and describes several embodiments, adaptations, variations, alternatives and uses of the aspects of the invention, including what is presently believed to be the best mode of carrying out the aspects of the invention. Additionally, it is to be understood that the aspects of the invention is not limited in its application to the details of construction and the arrangement of components set forth in the following description or illustrated in the drawings. The aspects of the invention are capable of other embodiments and of being practiced or carried out in various ways. Also, it will be understood that the phraseology and terminology used herein is for the purpose of description and should not be regarded as limiting.

Having described aspects of the invention in detail, it will be apparent that modifications and variations are possible without departing from the scope of aspects of the invention as defined in the appended claims. It is contemplated that various changes could be made in the above constructions, products, and methods without departing from the scope of aspects of the invention. In the preceding specification, various preferred embodiments have been described with reference to the accompanying drawings. It will, however, be evident that various modifications and changes may be made thereto, and additional embodiments may be implemented, without departing from the broader scope of the aspects of the invention as set forth in the claims that follow. The specification and drawings are accordingly to be regarded in an illustrative rather than restrictive sense.

Real-Time Hemodynamic Response Changes Tracking (RTHRC) Model

Figure 10A:
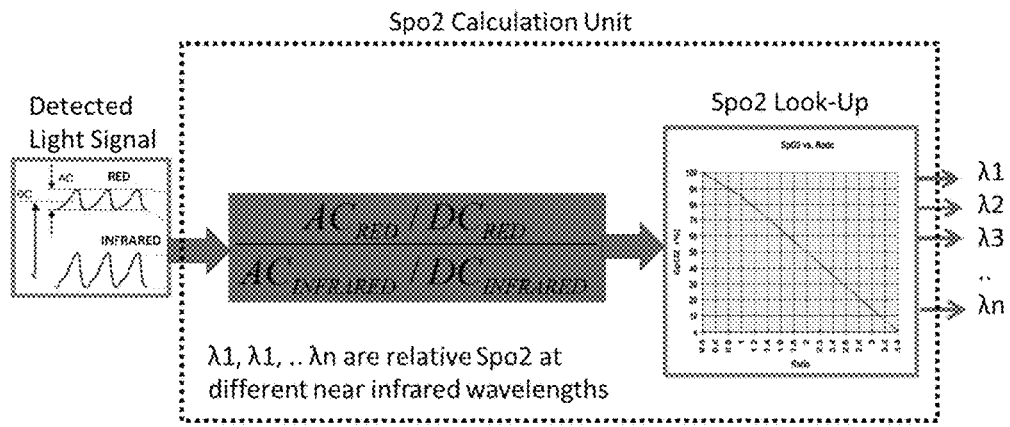
FIGS. 10A and 10B illustrate a general pipeline of Real-time hemodynamic response chances tracking (RTHRC).
Figure 10B:
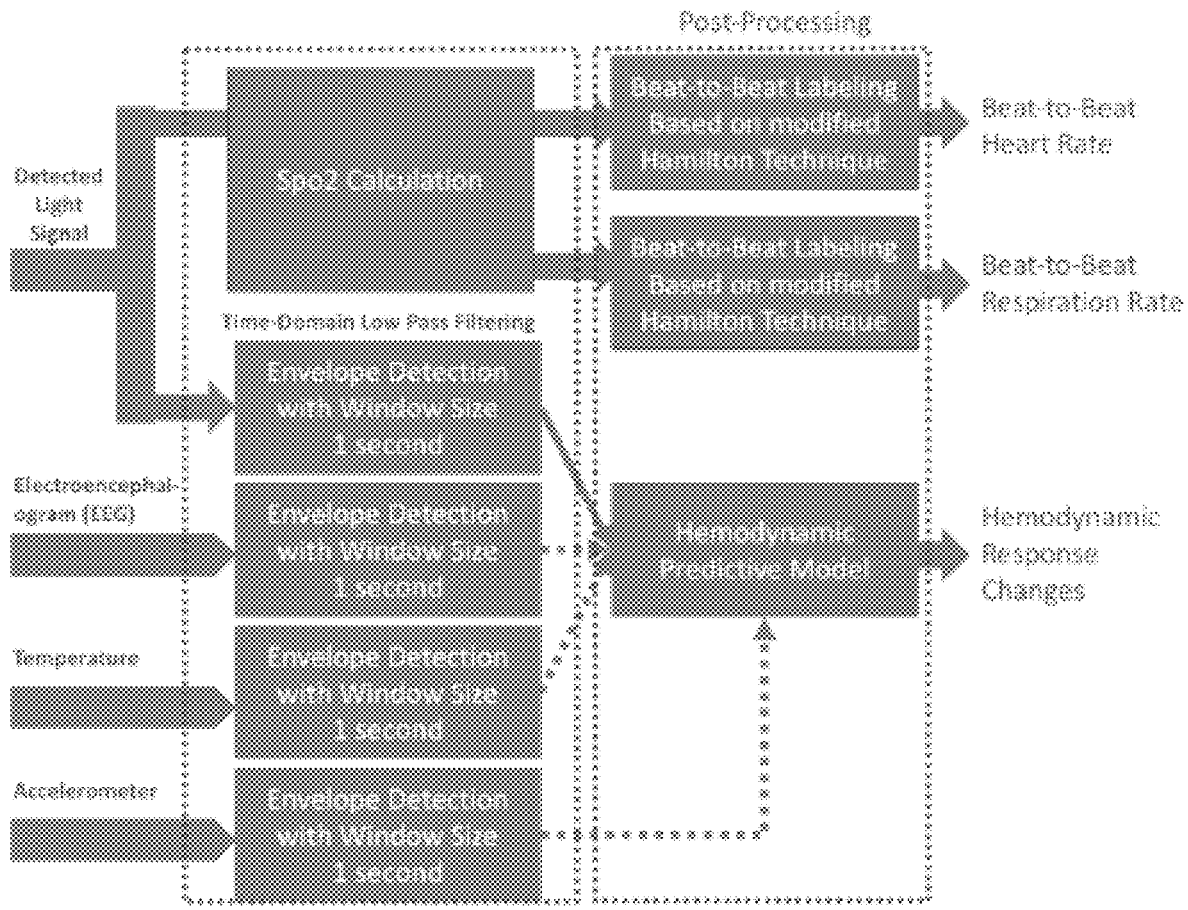

The RTHRC system and method comprises several steps and processing units to calculate several hemodynamic parameters including 1) heart (pulse) rate, 2) respiration rate and 3) hemodynamic response to an internal/external stimuli. FIGS. 10A and 10B show the general pipeline.

1—Spo2 Calculation Unit

Optical Sensing is a non-invasive measurement of the oxygen saturation (SpO2). Oxygen saturation is defined as the measurement of the amount of oxygen dissolved in blood, based on the detection of Hemoglobin and Deoxyhemoglobin.

Two or more different light wavelengths are used to measure the actual difference in the absorption spectra of HbO2 and Hb. The bloodstream is affected by the concentration of HbO2 and Hb, and their absorption coefficients are measured using red light and infrared light spectra. Pulse oximeter is an optical sensing based device which uses two wavelengths 660 nm (red light spectra) and 940 nm (infrared light spectra). Deoxygenated and oxygenated hemoglobin absorb different wavelengths. Deoxygenated hemoglobin (Hb) has a higher absorption at red light spectra and oxygenated hemoglobin (HbO2) has a higher absorption at infrared light spectra.

Figure 11:
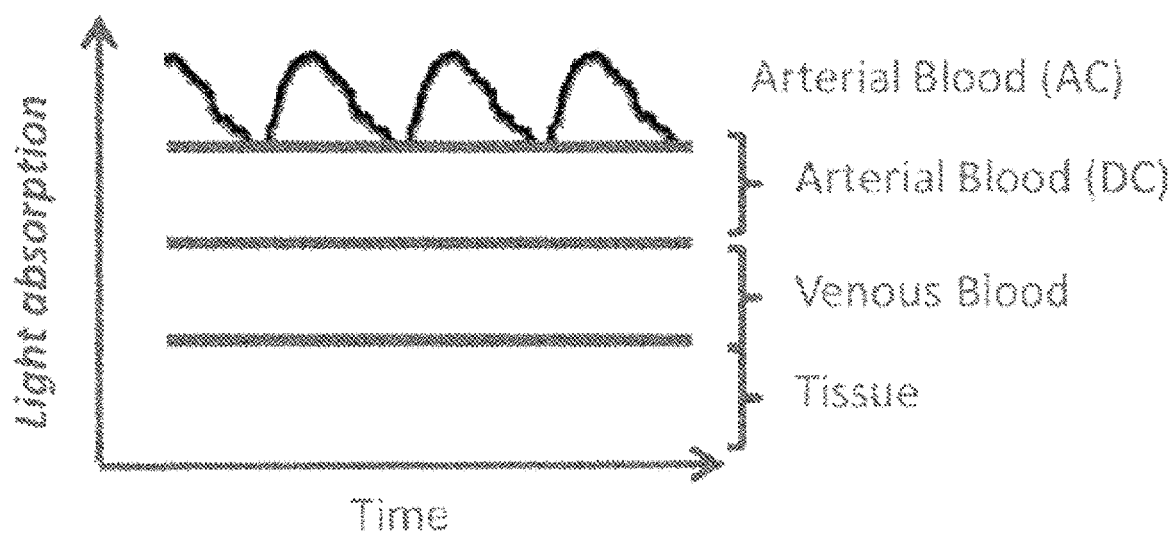
FIG. 11 illustrates a light absorption diagram.

A photodetector in the sensor perceives the non-absorbed light from the LEDs. This signal is inverted using hardware with operational amplifiers and the result is a signal like the one in FIG. 11. This signal represents the light that has been absorbed by the tissue and is divided in a DC component and an AC component. The DC component represents the light absorption of the tissue, venous blood, and non-pulsatile arterial blood. The AC component represents the pulsatile arterial blood.

Two or more wavelengths from the pulsatile-added volume of oxygenated arterial blood (AC/DC) and calculates the absorption ratio using the following equation.

$$\frac{AC_{RED}/DC_{RED}}{AC_{INFRARED}/DC_{INFRARED}} \qquad \text{Equation 1}$$

Figure 12:
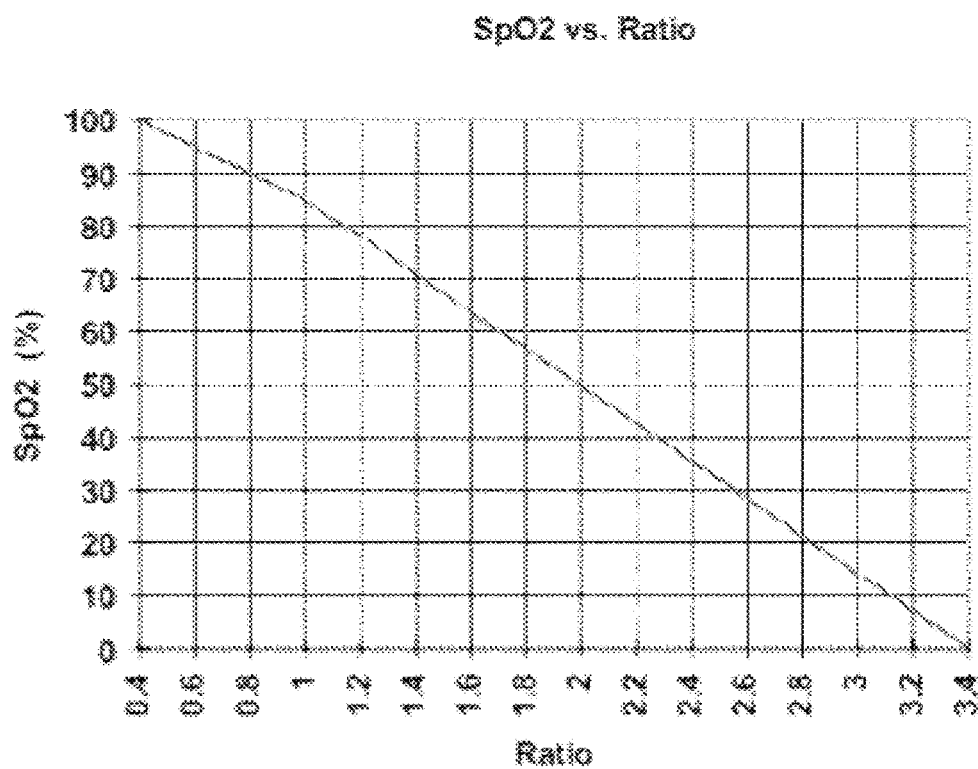
FIG. 12 illustrates how a ratio is used as the input to a "lookup table". The SpO2 value is the result of the "lookup" function.

SpO2 is taken out from a table stored on the memory calculated with empirical formulas (see FIG. 12). A ratio of 1 represents a SpO2 of 85%, a ratio of 0.4 represents SpO2 of 100%, and a ratio of 3.4 represents SpO2 of 0%. For more reliability, the table must be based on experimental measurements of healthy patients.

Another way for calculating SpO2 is driven from beer-lambert law by taking the AC component of only the signal and determinate ratio by using following equation. SpO2 is the value of RX100.

$$R = \frac{\log_{10}(I_{ac})\lambda 1}{\log_{10}(I_{ac})\lambda 2} \qquad \text{Equation 2}$$

Figure 13:
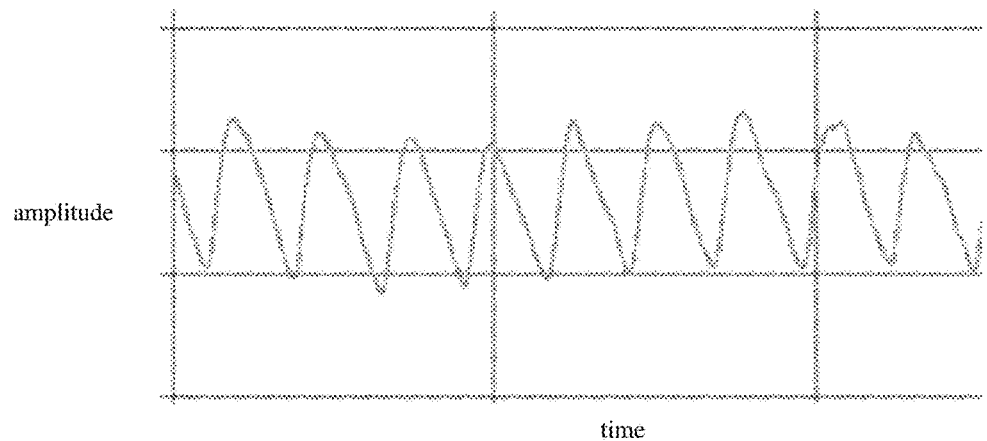
FIG. 13 illustrates a typical pulse oximetry signal.

$(Iac)\lambda_{RED}$=Light intensity at red light spectra and $(Iac)\lambda_{INFRARED}$=Light intensity at infrared light spectra, where only the AC level is present. A typical pulse oximetry signal is represented in FIG. 13. The signal represents the pulsatile arterial blood absorption. The beats per minute can be calculated using this signal.

2—Envelope Detection Based Time-Domain Low-Pass Filtering

Figure 14:
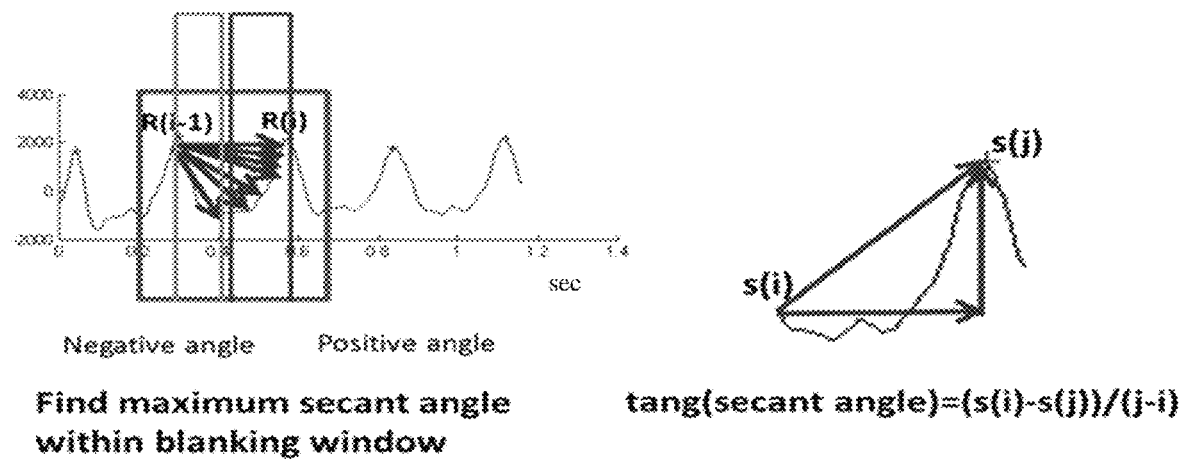
FIG. 14 illustrates detection of envelope of signal using secant angle. For Upper envelope detector searches for maximum secant angle within a user defined blanking window. For lower envelope it searches for minimum secant angle within the blanking window.

To detect upper and lower envelops of the raw spo2 data we use secant angle. This is needed to smooth data and eliminate carrier frequencies which are used to emit LEDs in different wavelengths. For Upper envelope detector searches for maximum secant angle within a user defined blanking window. For lower envelope it searches for minimum secant angle within the blanking window. Data samples for the upper envelope presents the timing of R-wave locations, while data samples for the lower envelope presents the timing of S-wave locations. FIG. 14 shows how to calculate envelope of a signal using secant angles.

3—Spot Pulse Annotation to Calculate Beat-to-Beat Heart/Respiration Rates

Figure 15:
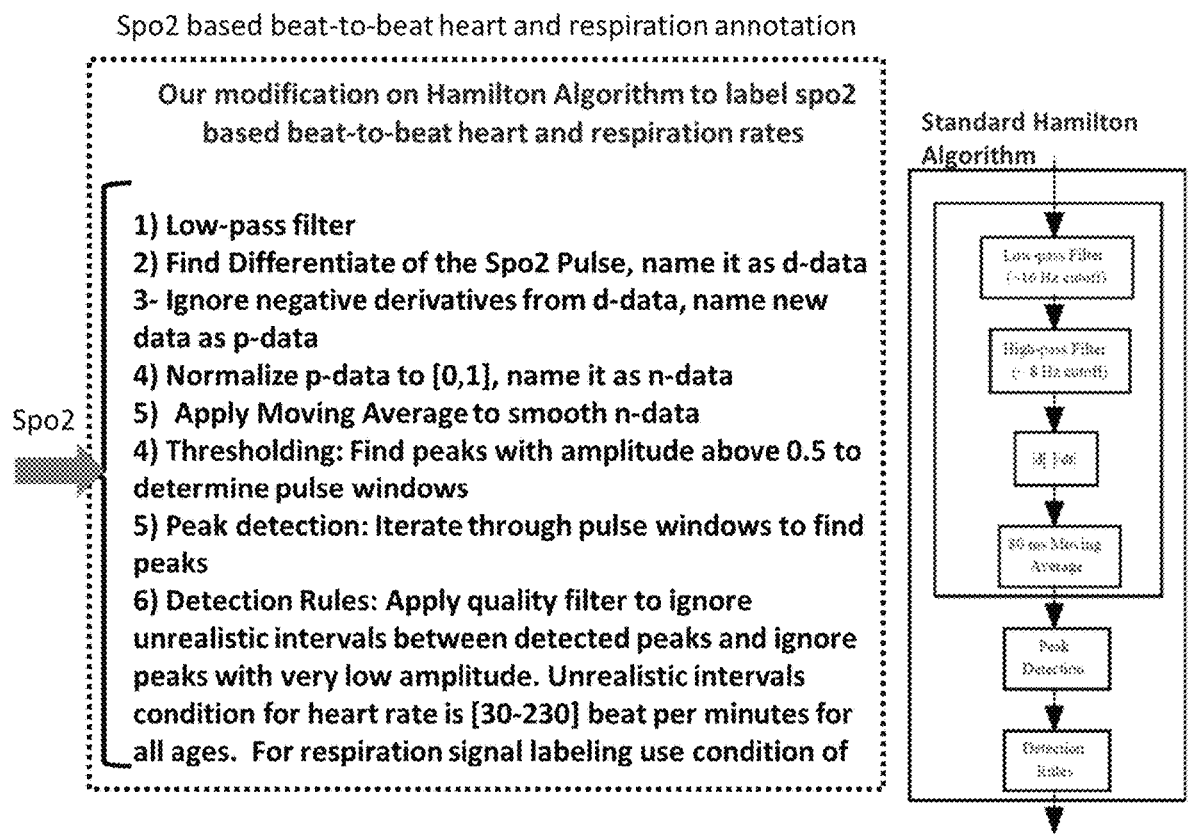
FIG. 15 illustrates Spo2 based beat-to-beat heart and respiration annotation.

An existing approach to annotate electrocardiogram (ECG) data is Hamilton technique. To calculate beat-to-beat heart/respiration rates we modified and improved the standard Hamilton algorithm. FIG. 15 shows steps to calculate spo2 based heart and respiration rates.

4—Hemodynamic Productive Modeling

Figure 16:
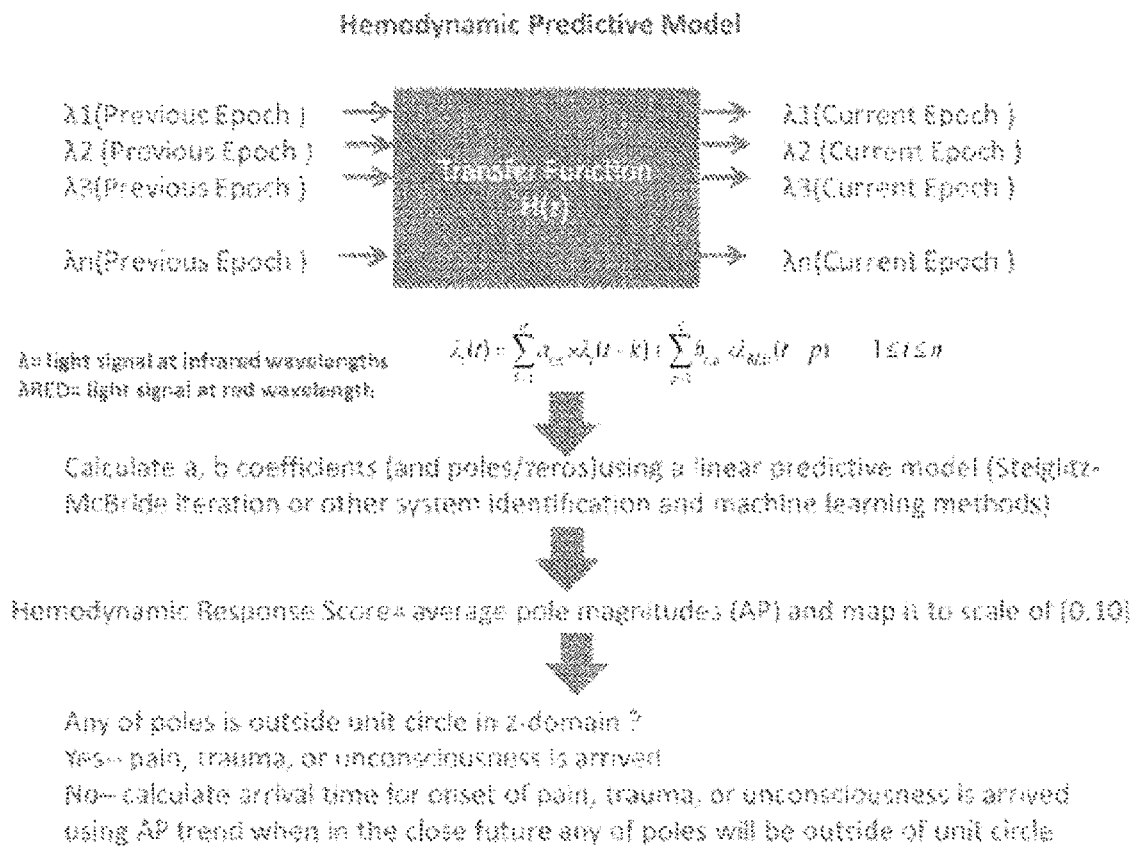
FIG. 16 illustrates a pipeline to predict hemodynamic changes using a predictive model.

To predict hemodynamic changes we use predictive model shown in FIG. 16, below. The system in FIG. 16 translates into the following equation $$\lambda_i(t) = \sum_{k=1}^{M} a_{i,k} \times \lambda_i(t-k) + \sum_{p=1}^{N} b_{i,p} \times \lambda_{RED}(t-p) \quad 1 \le i \le n \qquad \text{Equation 3}$$

Where t is time, $a_i$ and $b_i$ are the weights with which each light signal at red and infrared wavelength, respectively, contributes to the hemodynamic history; and M and N are the number of light signal samples included in the hemodynamic history. M and N are an order of IIR systems. M defines how many samples are included in the hemodynamic history. M and N are control parameters which controls the prediction by manufacturer or user.

Figure 17:
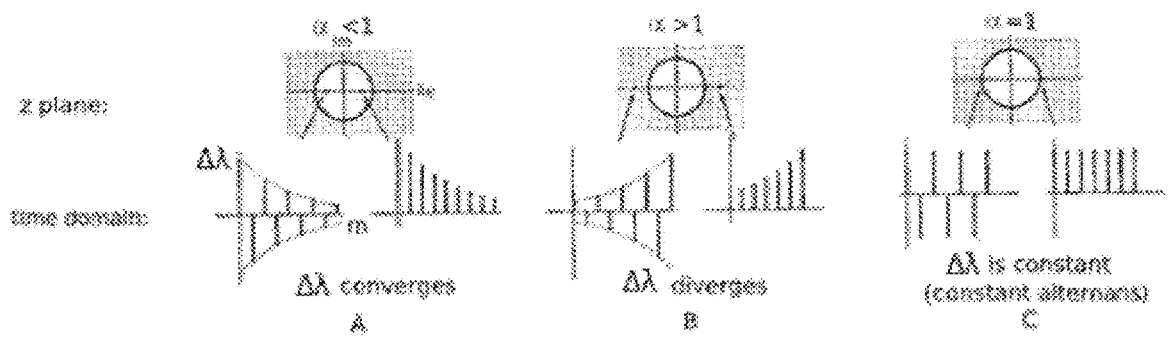
FIG. 17 illustrates different system behaviors for different locations of the pole ct. The location of the pole is shown in the z-plane, with the real (Re) and imaginary (Im) values of z being on the horizontal and vertical axes, respectively. The radius of the circle in the z-plane is 1 (unit circle). In the time domain, the behavior of the system is illustrated by the decreasing (A), increasing (B), or constant (C) magnitude of the oscillations following a perturbation (a premature or a delayed beat), depending on the location of a in the z-plane (inside, outside, or at the boundary of, the unit circle). m is the beat number, counted from the onset of perturbation.
Figure 18:
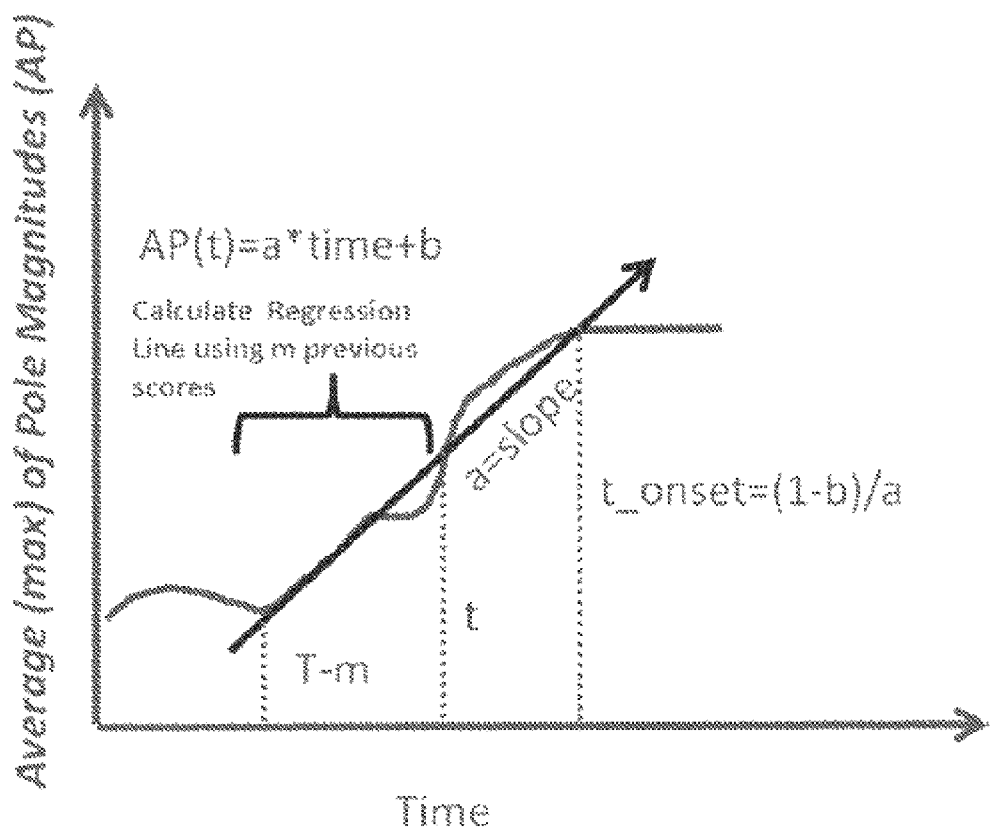
FIG. 18 illustrates a rough estimate arrival of unset of pain, trauma, or unconsciousness arrival by use of average and/or max of poles magnitudes (AP).

We propose to determine the values of M, N, $a_i$, $b_i$ (where i=1, . . . , M), and using a linear predictive model called linear model using Steiglitz-McBride iteration or any other artificial intelligence and system identification methods. In the z-domain, a system is represented as a transfer function. The transfer function H(z) representing Equation 3 in the z-domain is:

$$H(z) = \sum_{i=1}^{M} \frac{A_i}{z - \alpha_i}, \qquad \text{Equation 4}$$

where Ai and αi (i=1, . . . , M) are parameters derived from ai, bi (i=1, . . . , M), and M is the number of components in H(z), which is also the number of light signal samples in the hemodynamic history. In Equation 4, when z is set equal to αi, one obtains a pole of the system; a system has as many poles as there are values of α (i.e., M). According to the z-domain stability theory (bounded-input-bounded output concepts in electrical engineering) the system is unstable if a pole falls outside of the unit circle (|z|=1, see FIG. 17). FIG. 17 illustrates the different behaviors of the system for different locations of the pole. In FIG. 18, poles located within the unit circle (α<1) result in decreasing magnitude of the oscillations in light signal at infrared wavelengths (Δλ) following a perturbation of the system (a premature or a delayed beat).

In FIG. 17, panel B, where α>1, the magnitude of the oscillations caused by the perturbation increases. As mentioned above, the z-transform decomposes a system in the time domain into a series of power components with different bases. In the time domain, the unit circle (|z|=1) corresponds to a power component with a base of 1. A power component diverges when its base is bigger than 1, and converges if the base is smaller than 1. Computationally efficient implementations of stability analysis in z-domain are available thus we expect in achieve real-time execution of the method in the clinic.

To score hemodynamic response we use average of poles magnitudes and scale it from 0 to 10. For instance in the objective pain assessment hemodynamic response score has following interpretation:
0-1 No pain
2-3 Mild pain
4-5 Discomforting—moderate pain
6-7 Distressing—severe pain
8-9 Intense—very severe pain
10 Unbearable pain"

In the level of consciousness assessment hemodynamic response score has following interpretation:
0 Awake
2 Light/Moderate Sedation
4 General Anesthesia
6 Deep Hypnotic State
8 Burst Suppression
10 Fully unconscious Poles magnitudes are also are a sign of onset of pain arrival. If any of poles are outside unit circle that means onset of pain is above to start. Likelihood of pain arrival is estimated by following formula
Likelihood of Pain, Trauma, or Unconsciousness Arrival $$\text{Likelihood} = \frac{\text{Number of poles outside unit circle}}{\text{Total Number of poles}} \quad \text{Equation 5}$$

If average and/or max of poles magnitudes (AP) is gradually become closer to unit circle in z-domain space, the slope of trend is used to roughly estimate arrival of unset of pain, trauma, or unconsciousness arrival.

The relation between the above transfer function and partial differential equation (PDE) for infinite impulse response (IIR) of Equation 3 is based on known concepts. For example, see the following sources explaining implementation IIR based prediction systems and IIR filters.

[1] Sieiglitz, K., and L. E. McBride, "A Technique for the identification of Linear Systems," *IEEE Trans. Automatic Control*, Vol. AC-10 (1965), pp. 461-464.

[2] Oppenheim, Alan V.; Willsky, Alan S.; Nawab, Hamid; with S. Hamid (1998). *Signals and Systems*. Pearson Education. ISBN 0-13-814757-4.

What is claimed is:

1. A system for providing an indication of pain of a person, comprising:
a light source configured to be placed in proximity of the person's head, wherein the light source emits light in first and second wavelength regions of an electromagnetic spectrum;
an optical sensor configured to be placed in proximity of the person's head, wherein the optical sensor detects light in said first and second wavelength regions of the electromagnetic spectrum to provide a detection signal corresponding to a plurality of prior moments of time;
a controller configured to communicate with the optical sensor to receive said detection signal for said plurality of prior moments of time, the controller comprising a processor configured to provide oxygen content data of at least a portion of the person's brain proximate the light source and optical sensor based on detected light for the plurality of prior moments of time,
wherein the controller is further configured with a hemodynamic predictive model to provide said indication of pain based on said detection signal for said plurality of prior moments of time,
wherein the controller is further configured to apply a stability analysis on said hemodynamic predictive model to calculate a pain level of the person based on said stability analysis in real time by use of the detection signal as input to the hemodynamic predictive model for the plurality of prior moments of time to provide the indication of pain of the person, and
wherein said hemodynamic predictive model comprises a plurality of parameters that have values that are determined based on the detection signal corresponding to the plurality of prior moments of time,
wherein said hemodynamic predictive model is represented as a transfer function H(z) in a z-domain, and
wherein said stability analysis comprises an analysis of poles of said transfer function H(z).

2. The system of claim 1 wherein the light source emits infrared light and red light.

3. The system of claim 1 further comprising a display configured to communicate with the controller, the display configured to display the indication of pain.

4. The system of claim 1 wherein the processor scales the indication of pain to a value greater than or equal to 0 and less than or equal to 10.

5. The system of claim 1 wherein the processor categorizes the indication of pain into one of a plurality of categories, wherein the plurality of categories span a range from no pain to unbearable pain.

6. The system according to claim 1, wherein said stability analysis comprises determining a number of poles that fall outside of a unit circle in a z-plane compared to a total number of poles of said transfer function H(z).

7. A system for providing an indication of pain of a person, comprising:
a light source configured to be placed in proximity of the person's head, wherein the light source emits light in first and second wavelength regions of an electromagnetic spectrum;
an optical sensor configured to be placed in proximity of the person's head, wherein the optical sensor detects light in said first and second wavelength regions of the electromagnetic spectrum to provide a detection signal corresponding to a plurality of prior moments of time;
a controller configured to communicate with the optical sensor to receive said detection signal for said plurality of prior moments of time, the controller comprising a processor configured to provide oxygen content data of at least a portion of the person's brain proximate the light source and optical sensor based on detected light for the plurality of prior moments of time, wherein the controller is further configured with a hemodynamic predictive model to provide said indication of pain based on said detection signal for said plurality of prior moments of time, wherein the controller is further configured to apply a stability analysis on said hemodynamic predictive model to calculate a pain level of the person based on said stability analysis in real time by use of the detection signal as input to the hemodynamic predictive model for the plurality of prior moments of time to provide the indication of pain of the person, and wherein said hemodynamic predictive model comprises a plurality of parameters that have values that are determined based on the detection signal corresponding to the plurality of prior moments of time, wherein said hemodynamic predictive model is represented in a time domain as $$\lambda_i(t) = \sum_{k=1}^{M} a_{i,k} \times \lambda_i(t-k) + \sum_{p=1}^{N} b_{i,p} \times \lambda_{RED}(t-p)$$

where:

$1 \leq i \leq n$, n being the number of infrared wavelengths and i being an index over the infrared wavelengths;

$\lambda_i$ being a light signal at the $i^{th}$ infrared wavelength;

$\lambda_{RED}$=a light signal at a red light wavelength;

t=time;

$a_i$ and $b_i$ are weights with which each light signal at the red wavelength and the infrared wavelength, respectively, contributes to a hemodynamic history; and M and N are the number of light signal samples included in the hemodynamic history.

8. The system according to claim 7, wherein said hemodynamic predictive model in a z-domain is represented as $$H(z) = \sum_{i=1}^{M} \frac{A_i}{z - \alpha_i}$$

where $A_i$ and $\alpha_i$ (i=1, ..., M) are parameters derived from $a_i$, $b_i$ (i=1, ..., M), and M is a number of components in H(z).

* * * * *